United States Patent
Schaefer et al.

(10) Patent No.: US 12,161,785 B2
(45) Date of Patent: *Dec. 10, 2024

(54) EXTRACORPOREAL BLOOD TREATMENT FLOW RATE ADJUSTMENT

(71) Applicant: GAMBRO LUNDIA AB, Lund (SE)

(72) Inventors: Jonas Schaefer, St. Paul, MN (US); John O'Mahony, Plymouth, MN (US); Thomas Lendway, Vadnais Heights, MN (US)

(73) Assignee: Gambro Lundia AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 18/237,631

(22) Filed: Aug. 24, 2023

(65) Prior Publication Data

US 2024/0100231 A1    Mar. 28, 2024

Related U.S. Application Data

(63) Continuation of application No. 17/861,449, filed on Jul. 11, 2022, now Pat. No. 11,740,767, which is a (Continued)

(51) Int. Cl.
*G06F 3/048* (2013.01)
*A61M 1/14* (2006.01)
(Continued)

(52) U.S. Cl.
CPC .............. *A61M 1/14* (2013.01); *A61M 1/34* (2013.01); *A61M 1/3607* (2014.02);
(Continued)

(58) Field of Classification Search
CPC .... G06F 3/04817; G06F 3/0482; A61M 1/14; A61M 1/3607; A61M 1/3609; A61M 1/34; G16H 40/73
See application file for complete search history.

(56) References Cited

U.S. PATENT DOCUMENTS

| 4,942,514 A | 7/1990 | Miyagaki |
| 5,247,434 A | 9/1993 | Peterson |

(Continued)

FOREIGN PATENT DOCUMENTS

| CN | 101495163 | 7/2009 |
| CN | 102215942 | 10/2011 |

(Continued)

OTHER PUBLICATIONS

PCT Preliminary Examination Report for PCT/US2014/026215 dated Sep. 24, 2015 (15 pages).

(Continued)

*Primary Examiner* — Mahelet Shiberou
(74) *Attorney, Agent, or Firm* — Mueting Raasch Group

(57) ABSTRACT

Extracorporeal blood treatment systems and methods to display graphical user interfaces displaying a plurality of fluids areas, each including a flow rate, and displaying adjustment notifications proximate one or more fluid areas. For example, when a user adjusts a flow rate to a limit, one or more notifications may be displayed proximate other flow rates that may be adjusted to modify the limit.

20 Claims, 16 Drawing Sheets

Related U.S. Application Data continuation of application No. 17/151,503, filed on Jan. 18, 2021, now Pat. No. 11,385,769, which is a continuation of application No. 15/128,442, filed as application No. PCT/US2015/022633 on Mar. 26, 2015, now Pat. No. 10,895,957.

(60) Provisional application No. 61/972,713, filed on Mar. 31, 2014.

(51) Int. Cl.
*A61M 1/34* (2006.01)
*A61M 1/36* (2006.01)
*G06F 3/04817* (2022.01)
*G06F 3/0482* (2013.01)
*G16H 40/63* (2018.01)

(52) U.S. Cl.
CPC ....... *A61M 1/3609* (2014.02); *G06F 3/04817* (2013.01); *G06F 3/0482* (2013.01); *G16H 40/63* (2018.01); *A61M 2205/3334* (2013.01); *A61M 2205/3379* (2013.01); *A61M 2205/3393* (2013.01); *A61M 2205/50* (2013.01); *A61M 2205/502* (2013.01); *A61M 2205/505* (2013.01)

(56) References Cited

U.S. PATENT DOCUMENTS

| | | |
|---|---|---|
| 5,326,476 A | 7/1994 | Grogan |
| 5,486,286 A | 1/1996 | Peterson |
| 5,487,827 A | 1/1996 | Peterson |
| 5,581,687 A | 12/1996 | Lyle |
| 5,609,770 A | 3/1997 | Zimmerman |
| 5,620,608 A | 4/1997 | Rosa |
| 5,744,027 A | 4/1998 | Connell |
| 5,788,851 A | 8/1998 | Kenley |
| 5,858,239 A | 1/1999 | Kenley |
| 5,956,023 A | 9/1999 | Lyle |
| 6,146,523 A | 11/2000 | Kenley |
| 6,256,643 B1 | 7/2001 | Cork |
| 6,284,131 B1 | 9/2001 | Hogard |
| 6,363,290 B1 | 3/2002 | Lyle |
| 6,542,910 B2 | 4/2003 | Cork |
| 6,614,456 B1 | 9/2003 | Rzepkowski |
| 6,738,052 B1 | 5/2004 | Manke |
| 6,775,577 B2 | 8/2004 | Crnkovich |
| 6,953,323 B2 | 10/2005 | Childers |
| 7,029,456 B2 | 4/2006 | Ware |
| 7,033,539 B2 | 4/2006 | Krensky |
| 7,085,604 B2 | 8/2006 | Turney |
| 7,108,672 B2 | 9/2006 | Steele |
| 7,256,771 B2 | 8/2007 | Novak |
| 7,264,730 B2 | 9/2007 | Connell |
| 7,278,981 B2 | 10/2007 | Ellingboe |
| 7,303,540 B2 | 12/2007 | O'Mahony |
| 7,303,680 B2 | 12/2007 | Connell |
| 7,318,892 B2 | 1/2008 | Connell |
| 7,351,340 B2 | 4/2008 | Connell |
| 7,410,475 B2 | 8/2008 | Krensky |
| 7,585,286 B2 | 9/2009 | O'Mahony |
| 7,618,531 B2 | 11/2009 | Sugioka |
| 7,699,806 B2 | 4/2010 | Ware |
| 7,713,240 B2 | 5/2010 | Istoc |
| 7,891,625 B2 | 2/2011 | Chevallet |
| 8,012,114 B2 | 9/2011 | Daniel |
| 8,057,419 B2 | 11/2011 | Ellingboe |
| 8,095,390 B2 | 1/2012 | Bluemler |
| 8,298,167 B2 | 10/2012 | Peters |
| 8,317,750 B2 | 11/2012 | Ware |
| 8,323,503 B2 | 12/2012 | Levin |
| 8,343,129 B2 | 1/2013 | Falkvall |
| 8,376,999 B2 | 2/2013 | Busby |
| 8,382,696 B2 | 2/2013 | Beiriger |
| 8,409,441 B2 | 4/2013 | Wilt |
| 8,425,487 B2 | 4/2013 | Beiriger |
| 8,485,998 B2 | 7/2013 | Moll |
| 8,506,522 B2 | 8/2013 | Britton |
| 8,529,496 B2 | 9/2013 | Britton |
| 8,543,420 B2 | 9/2013 | Darby |
| 8,562,584 B2 | 10/2013 | Beiriger |
| 8,587,516 B2 | 11/2013 | Kopychev |
| 8,632,485 B2 | 1/2014 | Schlaeper |
| 8,687,003 B2 | 4/2014 | Dalesch |
| 8,698,741 B1 | 4/2014 | Wang |
| 8,769,625 B2 | 7/2014 | Wang |
| 8,856,668 B2 | 10/2014 | Niesslein |
| 8,870,812 B2 | 10/2014 | Alberti |
| 8,924,458 B2 | 12/2014 | Levin |
| 8,992,777 B2 | 3/2015 | Doyle |
| 9,005,150 B2 | 4/2015 | Ware |
| 9,084,855 B2 | 7/2015 | Ware |
| 9,132,061 B2 | 9/2015 | Beiriger |
| 9,138,379 B2 | 9/2015 | Beiriger |
| 9,138,526 B2 | 9/2015 | Ware |
| 9,165,112 B2 | 10/2015 | Doyle |
| 9,254,357 B2 | 2/2016 | Falkvall |
| 9,283,145 B2 | 3/2016 | Beiriger |
| 9,293,110 B2 | 3/2016 | Dolgos |
| 9,311,448 B2 | 4/2016 | Gruendken |
| 9,833,556 B2 | 12/2017 | Olde |
| 2002/0067373 A1 | 6/2002 | Roe |
| 2002/0085952 A1 | 7/2002 | Ellingboe |
| 2003/0222872 A1 | 12/2003 | Lin |
| 2004/0084372 A1 | 5/2004 | Connell |
| 2005/0022274 A1 | 1/2005 | Campbell |
| 2005/0025644 A1 | 2/2005 | Ford |
| 2005/0045540 A1 | 3/2005 | Connell |
| 2005/0070837 A1 | 3/2005 | Ferrarini |
| 2005/0256444 A1 | 11/2005 | O'Mahony |
| 2006/0229557 A1 | 10/2006 | Fathallah |
| 2006/0258985 A1 | 11/2006 | Russell |
| 2007/0083152 A1 | 4/2007 | Williams |
| 2007/0112603 A1 | 5/2007 | Kauthen |
| 2007/0118405 A1 | 5/2007 | Campbell |
| 2007/0138069 A1 | 6/2007 | Roncadi |
| 2007/0235376 A1 | 10/2007 | Daniel |
| 2008/0004818 A1 | 1/2008 | Zaleski |
| 2008/0027368 A1 | 1/2008 | Kollar |
| 2008/0077069 A1 | 3/2008 | O'Mahony |
| 2008/0077072 A1 | 3/2008 | Keenan |
| 2008/0161751 A1 | 7/2008 | Plahey |
| 2008/0221495 A1 | 9/2008 | Steffens |
| 2008/0255438 A1 | 10/2008 | Saidara |
| 2008/0256489 A1 | 10/2008 | Maurer |
| 2008/0287922 A1 | 11/2008 | Panduro |
| 2008/0300572 A1 | 12/2008 | Rankers |
| 2009/0008306 A1 | 1/2009 | Cicchello |
| 2009/0113335 A1 | 4/2009 | Sandoe |
| 2010/0010330 A1 | 1/2010 | Rankers |
| 2010/0049114 A1 | 2/2010 | Brown |
| 2010/0076364 A1 | 3/2010 | O'Mahony |
| 2010/0121246 A1 | 5/2010 | Peters |
| 2010/0137693 A1 | 7/2010 | Porras |
| 2010/0192686 A1 | 8/2010 | Kamen |
| 2011/0001766 A1 | 1/2011 | Hua |
| 2011/0017667 A1 | 1/2011 | Delmage |
| 2011/0077586 A1 | 3/2011 | Plahey |
| 2011/0167366 A1 | 7/2011 | Wagner |
| 2012/0154264 A1 | 6/2012 | Wang |
| 2012/0185267 A1 | 7/2012 | Kamen |
| 2012/0228226 A1 | 9/2012 | Castellarnau |
| 2012/0109037 A1 | 11/2012 | Ellingboe |
| 2012/0277651 A1 | 11/2012 | Gruendken |
| 2013/0172806 A1 | 7/2013 | Griessmann |
| 2013/0293570 A1 | 11/2013 | Dolgos |
| 2013/0298062 A1 | 11/2013 | Dolgos |
| 2013/0324804 A1 | 12/2013 | Mckeown |
| 2013/0345666 A1 | 12/2013 | Panduro |
| 2014/0107835 A1 | 4/2014 | Biasi |
| 2014/0121845 A1 | 5/2014 | Mueller |
| 2014/0205981 A1 | 7/2014 | Ryder |
| 2014/0298171 A1 | 10/2014 | Wang |

(56) References Cited

U.S. PATENT DOCUMENTS

| | | |
|---|---|---|
| 2015/0022334 A1 | 1/2015 | Guillory |
| 2015/0100009 A1 | 4/2015 | Bearss |
| 2015/0119805 A1 | 4/2015 | Blomquist |
| 2015/0342537 A1 | 12/2015 | Taylor |
| 2016/0022892 A1 | 1/2016 | Eifler |
| 2016/0055303 A1 | 2/2016 | Keller |
| 2016/0058933 A1* | 3/2016 | Ballantyne ............ G06F 21/565 210/85 |
| 2016/0231396 A1 | 8/2016 | Sunaga |
| 2016/0334261 A1 | 11/2016 | Wilson, III |
| 2017/0102846 A1 | 4/2017 | Ebler |
| 2018/0095640 A1 | 4/2018 | Albright |
| 2018/0150614 A1 | 5/2018 | Sokolovskyy |

FOREIGN PATENT DOCUMENTS

| | | |
|---|---|---|
| CN | 102652843 | 9/2012 |
| CN | 102686251 | 9/2012 |
| DE | 19742633 | 4/1999 |
| DE | 10013666 | 4/2006 |
| DE | 102010056605 | 6/2012 |
| EP | 0668793 | 4/2000 |
| EP | 597817 | 7/2003 |
| EP | 1191342 | 10/2007 |
| EP | 1509261 | 12/2007 |
| EP | 2126768 | 12/2009 |
| EP | 1847282 | 3/2011 |
| EP | 2314333 | 7/2012 |
| EP | 2659918 | 11/2013 |
| EP | 2659919 | 12/2014 |
| JP | H11262522 | 9/1999 |
| WO | WO 02/026286 | 4/2002 |
| WO | WO 2004/069311 | 8/2004 |
| WO | WO 2005/039671 | 5/2005 |
| WO | WO 2006/014162 | 2/2006 |
| WO | WO 2007/124069 | 11/2007 |
| WO | WO 2007/144427 | 12/2007 |
| WO | WO 2008/074316 | 6/2008 |
| WO | WO 2011/002853 | 1/2011 |
| WO | WO 2014/151669 | 9/2014 |

OTHER PUBLICATIONS

PCT International Search Report and Written Opinion for PCT/US2014/026215 dated Oct. 1, 2014 (18 pages).

ip.com, Extracorporeal Blood Processing Information Management System Including Regulatory Compliance, Aug. 14, 2006.

International Preliminary Report on Patentability for Application No. PCT/US2015/022633 dated Oct. 13, 2016 (16 pages).

Office Action issued in Brazil for Application No. 112016022215-6 dated Mar. 12, 2020 (5 pages).

International Search Report and Written Opinion for Application No. PCT/US2015/022633 dated Jun. 10, 2015 (10 pages).

* cited by examiner

EXTRACORPOREAL BLOOD TREATMENT FLOW RATE ADJUSTMENT

CROSS-REFERENCE

This application is a continuation of U.S. application Ser. No. 17/861,449, filed Jul. 11, 2022, which is a continuation of U.S. application Ser. No. 17/151,503, filed Jan. 18, 2021, now U.S. Pat. No. 11,385,769, which is a continuation of U.S. application Ser. No. 15/128,442, filed Sep. 23, 2016, now U.S. Pat. No. 10,895,957, and which is a U.S. National Stage Application of International Application No. PCT/US2015/022633, filed Mar. 26, 2015 and published in English on Oct. 8, 2015 as International Publication No. WO 2014/153253 A1, which claims the benefit under 35 U.S.C. 119 (e) of U.S. Provisional Application Ser. No. 61/972,713, filed on Mar. 31, 2014, which are is incorporated herein by reference in their entireties.

BACKGROUND

The disclosure herein relates to extracorporeal blood treatment. More particularly, the disclosure relates to graphical user interfaces displaying a plurality of fluid areas, each including an adjustable flow rate.

Extracorporeal blood treatment may refer to taking blood from a patient, treating the blood outside the patient, and returning the treated blood to the patient. Extracorporeal blood treatment is typically used to extract undesirable matter or molecules from the patient's blood, and/or to add beneficial matter or molecules to the blood. Extracorporeal blood treatment may be used with patients incapable of effectively eliminating matter from their blood, for example, in the case of a patient who is suffering from temporary or permanent kidney failure. These and other patients may, for instance, undergo extracorporeal blood treatment to add to or to eliminate matter from their blood, to maintain an acid-base balance or to eliminate excess body fluids.

In a variety of extracorporeal blood treatments, one or more fluids, or liquids, may be supplied to the extracorporeal blood treatment apparatus for use during the treatments and one or more fluids may be collected as a part of the treatments. Adjustment of flow rates may be used to control the treatment process.

Due to the nature of extracorporeal blood treatments, adjusting a flow rate of one pump often has a direct effect on the flow rate of another. For example, either the other flow is directly adjusted or the limits to which it may be changed to may be affected.

SUMMARY

One or more exemplary embodiments of the present disclosure describes systems and methods that provide adjustment notifications proximate one or more fluid areas on a graphical user interface when one or more flow rates are modified or adjusted. For example, when a flow rate is adjusted to a limit, one or more adjustment notifications may be displayed proximate one or more other fluid areas to indicate that the flow rates of the one or more other fluid areas may need to be adjusted to allow adjustment of the limit of the flow rate being adjusted.

One exemplary extracorporeal blood treatment system may include a display apparatus and a computing apparatus. The display apparatus may include a graphical user interface that is configured to depict a fluids region. The computing apparatus may be operatively coupled to the display apparatus and configured to display on the graphical user interface a fluids region including a plurality of fluid areas. Each fluid area of the plurality of fluid areas may include a flow rate and at least one limit value (e.g., an upper limit and a lower limit), wherein the flow rate is depicted in the fluid area. The computing apparatus may be further configured to allow a user to adjust the flow rate of a selected fluid area of the plurality of fluid areas and display, when the flow rate of the selected fluid area has been adjusted such that the at least one limit of the selected fluid area has been reached, an adjustment notification proximate one or more other fluid areas of the plurality of fluid areas. Further, the one or more other fluid areas may be adjustable to modify the at least one limit of the selected fluid area.

One exemplary method for an extracorporeal blood treatment system may include providing a graphical user interface including a fluids region, and displaying on the graphical user interface a fluids region including a plurality of fluid areas. Each fluid area of the plurality of fluid areas may include a flow rate and at least one limit value (e.g., an upper limit and a lower limit), wherein the flow rate is depicted in the fluid area. The exemplary method may further include allowing a user to adjust the flow rate of a selected fluid area of the plurality of fluid areas and displaying, when the flow rate of the selected fluid area has been adjusted such that the at least one limit of the selected fluid area has been reached, an adjustment notification proximate one or more other fluid areas of the plurality of fluid areas. Further, the one or more other fluid areas may be adjustable to modify the at least one limit of the selected fluid area.

In one or more embodiments, an adjustment information area (e.g., including at least one of a description of the at least one limit, a description of the one or more other fluid areas, and a description of an action required to be performed on the one or more other fluid areas to modify the at least one limit of the selected fluid area) may be displayed proximate the selected fluid area of the plurality of fluid areas including information relevant to the one or more other fluid areas of the plurality of fluid areas that are adjustable to modify the at least one limit of the selected fluid area when the flow rate of the selected fluid area has been adjusted such that the at least one limit of the selected fluid area has been reached.

In one or more embodiments, the adjustment notification may include an icon indicating an increase or decrease of the flow rate of the one or more other fluid areas to modify the at least one limit of the selected fluid area and/or an animation. In one or more embodiments, each fluid area of the plurality of fluid areas may further include an icon representing one of a pump and a syringe.

In one or more embodiments, the selected fluid area may further include a previous flow rate that is the flow rate prior to adjustment, and the previous flow rate may be depicted in the selected fluid area when a user adjusts the flow rate of the selected fluid area. In one or more embodiments, the selected fluid area of the plurality of fluid areas may further include an adjustment area configured to allow a user to adjust the flow rate of the selected fluid area and the adjustment area may display the at least one limit and a graphical indication of flow rate of the selected fluid area with respect to the at least one limit.

In one or more embodiments, graphical representations of fluid connections between one or more fluid areas of the plurality of fluid areas and a change region may be displayed prior to a user adjusting the flow rate of a fluid area of the plurality of fluid areas. When a user selects the change region to initiate an action associated with at least one fluid area of the plurality of fluid areas, the graphical representations of fluid connections may be configured to vanish.

In one or more embodiments, the plurality of fluid areas correspond to one or more of pre blood pump, effluent, citrate, blood flow rate, patient fluid removal, dialysate, replacement fluid, anticoagulation, patient plasma loss, and calcium.

One extracorporeal blood treatment system may include display apparatus and computing apparatus operatively coupled to the display apparatus. The display apparatus may include a graphical user interface configured to depict a fluids region. The computing apparatus may be configured to display on the graphical user interface a fluids region including a plurality of fluid areas. Each fluid area of the plurality of fluid areas may include a flow rate depicted in the fluid area. The computing apparatus may be further configured to display graphical representations of fluid connections between one or more fluid areas of the plurality of fluid areas prior to a user adjusting the flow rate of a fluid area of the plurality of fluid areas and remove the graphical representations of fluid connections from the graphical user interface when a user initiates an action associated with at least one fluid area of the plurality of fluid areas.

One exemplary method for an extracorporeal blood treatment system may include providing a graphical user interface including a fluids region, and displaying on the graphical user interface a fluids region including a plurality of fluid areas. Each fluid area of the plurality of fluid areas may include a flow rate depicted in the fluid area. The exemplary method may further include displaying graphical representations of fluid connections between one or more fluid areas of the plurality of fluid areas prior to a user adjusting the flow rate of a fluid area of the plurality of fluid areas, displaying on the graphical user interface a change region, and removing the graphical representations of fluid connections from the graphical user interface when a user initiates an action associated with at least one fluid area of the plurality of fluid areas.

In one or more embodiments, the graphical user interface may further include a change region configured, upon selection by the user, to allow an action associated with at least one fluid area of the plurality of fluid areas. In one or more embodiments, the action associated with at least one fluid area of the plurality of fluid areas may include one of a flow rate adjustment and a reservoir change.

One extracorporeal blood treatment system may include a display apparatus and a computing apparatus operatively coupled to the display apparatus. The display apparatus may include a graphical user interface configured to depict a fluids region. The computing apparatus may be configured to display on the graphical user interface a fluids region including a plurality of fluid areas. Each fluid area of the plurality of fluid areas may include a flow rate depicted in the fluid area. The computing apparatus may be further configured to display graphical representations of fluid connections between one or more fluid areas of the plurality of fluid areas prior to a user adjusting the flow rate of a fluid area of the plurality of fluid areas and graphically modify the graphical representations of fluid connections when a user initiates an action associated with at least one fluid area of the plurality of fluid areas.

One exemplary method for an extracorporeal blood treatment system may include providing a graphical user interface including a fluids region and displaying on the graphical user interface a fluids region including a plurality of fluid areas. Each fluid area of the plurality of fluid areas may include a flow rate depicted in the fluid area. The exemplary method may further include displaying graphical representations of fluid connections between one or more fluid areas of the plurality of fluid areas prior to a user adjusting the flow rate of a fluid area of the plurality of fluid areas and graphically modifying the graphical representations of fluid connections when a user initiates an action associated with at least one fluid area of the plurality of fluid areas.

In one or more embodiments, the graphical user interface may be configured to allow the user to select the fluids region to initiate an action associated with at least one fluid area of the plurality of fluid areas. In one or more embodiments, the graphical user interface may be configured to allow the user to select a selected fluid area of the plurality of fluid areas to initiate an action associated with the selected fluid area of the plurality of fluid areas. In one or more embodiments, the one or more fluid areas of the plurality of fluid areas other than the selected area may also be graphically modified and non-functional when the user selects the selected fluid area of the plurality of fluid areas to initiate an action associated with the selected fluid area of the plurality of fluid areas.

In one or more embodiments, graphically modify the graphical representations of fluid connections may include darkening the graphical representations of fluid connections. In one or more embodiments, the action associated with at least one fluid area of the plurality of fluid areas may include one of a flow rate adjustment and a reservoir change.

One or more exemplary embodiments may be described as graphic interfaces that provide live feedback to an operator, or user, regarding adjusting flow rates and the relationship they have with each other. Flow rates may be adjusted before a treatment is started, during the course of a treatment, and as a way of creating a preset profile for use during a future treatment. Flow rates may be adjusted and then accepted by pressing, or selecting, an "Accept" area proximate a lower left-hand corner of the graphic interface. Further, the flow rates may be adjusted by using a control on the interface and may be adjusted one at a time. As a flow rate is adjusted, it can change the rate of flow of another flow rate. Additionally, the limits of the flow rate may be affected by the current settings of other flow rates. In one or more embodiments, the limits may be displayed on the graphic control region that the operator is adjusting.

Reaching a limit of a flow rate can be caused by several factors. For example, in a three way flow rate example, a limit on the total flow may cause a limit of fluid that can pass through a portion of the set tubing. As more than one solution is passing through that portion of the set the combination of more than one flow rate amounts to the total flow. Hitting the limit of a flow rate can be caused by its combination with two other flow rates. Lowering one of the two other flows can increase the limit on the flow being adjusted. When an operator, or user, hits a limit, the graphic user interface (GUI) may react by displaying a dialog stating the reason the limit was reached. Further, an arrow pointing towards a line may be displayed in the flow rate button indicating the operator has reached a hard limit. Additionally, the other flow rates that are affecting the limit may be identified by flashing arrows indicating which direction they can be adjusted to further increase the range of the limit. If more information is needed regarding the limit, a down arrow on the dialog can be pressed to display additional text regarding the limit and actions an operator can take. Adjusting any of the three flow rates affecting the limit will cause the dialog and arrows to disappear.

The exemplary systems and methods described herein may provide a safety net and help operators remain inside a comfortable range when entering a treatment. Different types of constraints come into effect depending on the flow rate being adjusted and a helpful indication may assist to notify the operator what happened. Further, providing live feedback when a constraint is reached may allow an operator to better understand the flows they are adjusting, the connection between them, and how to further adjust accordingly.

The above summary of the present disclosure is not intended to describe each embodiment or every implementation thereof. Advantages, together with a more complete understanding of the present disclosure, will become apparent and appreciated by referring to the following detailed description and claims taken in conjunction with the accompanying drawings.

DETAILED DESCRIPTION OF EXEMPLARY EMBODIMENTS

Figure 1:
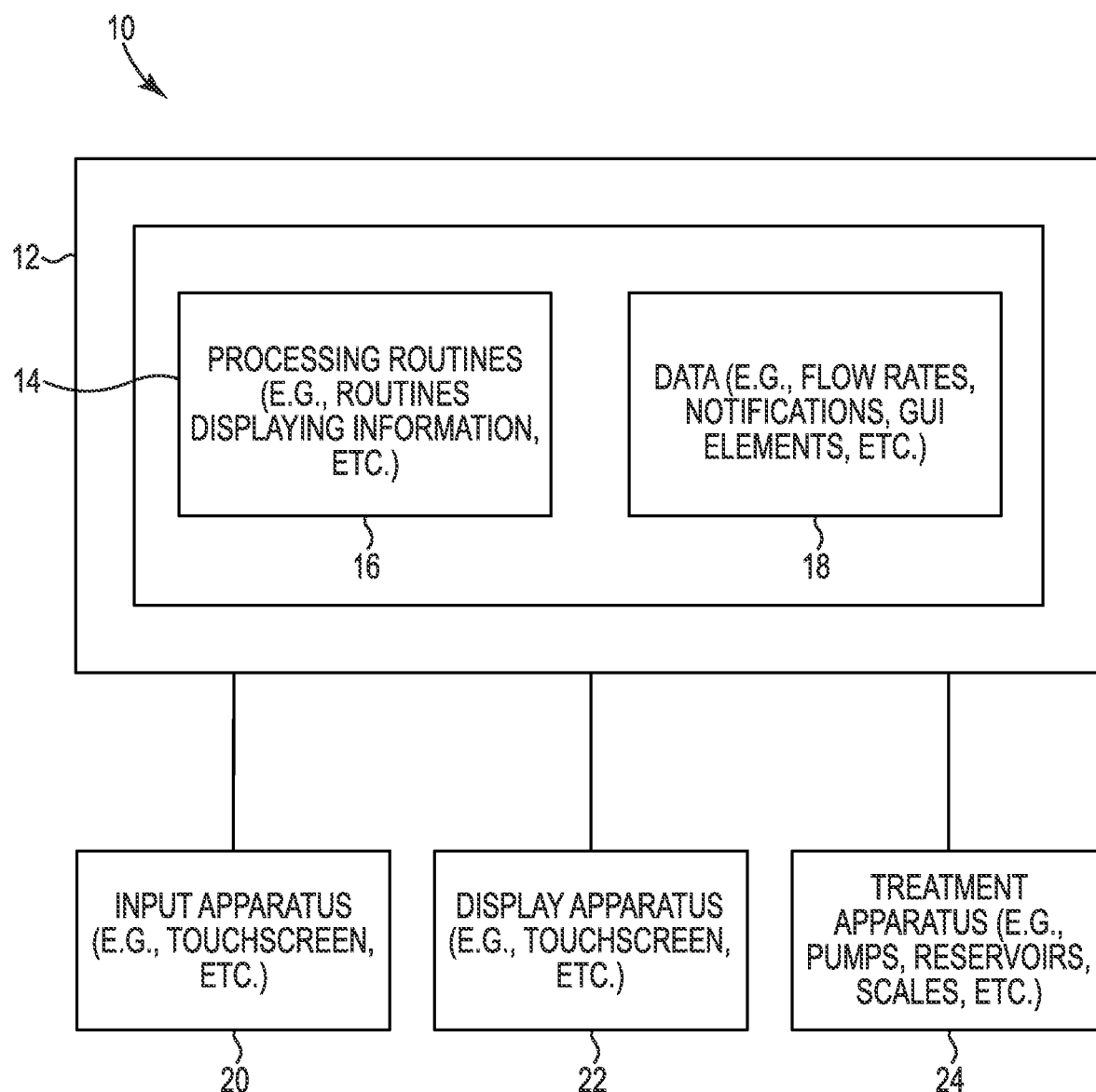
FIG. 1 is a block diagram of an exemplary extracorporeal blood treatment system including input apparatus, display apparatus, and treatment apparatus that may utilize the graphical user interfaces and methods described herein.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary systems and methods providing graphical user interfaces for use in extracorporeal blood treatments shall be described with reference to FIGS. 1-16. It will be apparent to one skilled in the art that elements or processes from one embodiment may be used in combination with elements or processes of the other embodiments, and that the possible embodiments of such systems and methods using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

The exemplary systems and/or methods may include graphically displaying a fluids region depicting one or more fluid areas having pump elements, flow rate limits, flow rate buttons, reservoir elements, etc. The flow rate of a fluid represented by a fluid area may be adjusted by, e.g., selecting a pump element. The flow rate of each fluid may be limited (e.g., upper and lower flow rate limits) based on multiple factors including but not limited to the other flow rates of the extracorporeal blood treatment system (e.g., shown by the other fluid areas). When a selected flow rate is adjusted to a limit, or the limit has been reached, the exemplary systems and/or methods may display adjustment notifications proximate one or more fluid areas that are adjustable to modify the limit of the selected flow rate.

The fluids region of the exemplary graphical user interfaces described herein may directly mimic the actual connections on and/or in an extracorporeal blood treatment system, and the association between the fluid areas and the actual physical components may allow an operator, or user, to more easily understand the pumps and reservoirs as well as their relationship to the system overall. Further, by displaying reservoirs on the graphical user interface that drain and fill in a similar way as the actual physical reservoirs, an operator may more easily accept feedback from the interface as being trustworthy. For example, the connection and association of the pump elements and the reservoir elements, as well as the notifications proximate thereto, and the various reservoir and notification "states" may create a user experience that more accurately reflects the system, may continuously instruct the operator, and may provide a visual representation of the prescription being delivered to the patient.

An exemplary extracorporeal blood treatment system 10 depicted in FIG. 1 may be used to execute, or perform, the exemplary methods and/or processes described herein. In at least one embodiment, the system 10 may be a machine for the extracorporeal treatment of blood. The system 10 could, for example, alternatively be a blood processing device or a blood component preparation device or other medical apparatus for fluid delivery/collection.

As shown, the exemplary extracorporeal blood treatment system 10 includes computing apparatus 12. The computing apparatus 12 may be configured to receive input from input apparatus 20 and transmit output to display apparatus 22. Further, the computing apparatus 12 may include data storage 14. Data storage 14 may allow for access to processing programs or routines 16 and one or more other types of data 18 that may be employed to carry out exemplary methods and/or processes (e.g., adjusting treatments, adjusting flow rates, calculating flow rates, determining flow rates dependent on other flow rates, running a treatment, notifying operator, or users, of problems, displaying status information, etc.) for use in performing extracorporeal blood treatments. For example, the computing apparatus 12 may be configured to display a fluids region on an exemplary graphical user interface displayed by the display apparatus 22 including one or more fluid areas, each having a flow rate associated therewith (e.g., which will be described further herein with respect to FIGS. 3-16).

The computing apparatus 12 may be operatively coupled to the input apparatus 20 and the display apparatus 22 to, e.g., transmit data to and from each of the input apparatus 20 and the display apparatus 22. For example, the computing apparatus 12 may be electrically coupled to each of the input apparatus 20 and the display apparatus 22 using, e.g., analog electrical connections, digital electrical connections, wireless connections, bus-based connections, etc. As described further herein, an operator may provide input to the input apparatus 20 to manipulate, or modify, one or more graphical depictions displayed on the display apparatus 22 to select and adjust one or more flow rates, etc. during, before, or after any extracorporeal blood treatments.

Further, various devices and apparatus may be operatively coupled to the computing apparatus 12 to be used with the computing apparatus 12 to perform one or more extracorporeal procedures/treatments as well as the functionality, methods, and/or logic described herein. As shown, the system 10 may include input apparatus 20, display apparatus 22, and treatment apparatus 24 operatively coupled to the computing apparatus 12 (e.g., such that the computing apparatus 12 may be configured to use information, or data, from the apparatus 20, 22, 24 and provide information, or data, to the apparatus 20, 22, 24). The input apparatus 20 may include any apparatus capable of providing input to the computing apparatus 12 to perform the functionality, methods, and/or logic described herein.

For example, the input apparatus 20 may include a touchscreen (e.g., capacitive touchscreen, a resistive touchscreen, a multi-touch touchscreen, etc.), a mouse, a keyboard, a trackball, etc. A touchscreen may overlay the display apparatus 22 such that, e.g., an operator may use the touchscreen to interact (e.g., by touch) with a graphical user interface displayed on the display apparatus. The input apparatus 20 may allow an operator to interact with a graphical user interface including a fluids region containing, or depicting, one or more fluid areas, each including information related to a different fluid to, e.g., adjust a flow rate of each fluid, etc. when used in conjunction with the display apparatus 22 (e.g., displaying the graphical user interface).

The display apparatus 22 may include any apparatus capable of displaying information to an operator, such as a graphical user interface, etc., to perform the functionality, methods, and/or logic described herein. For example, the display apparatus 22 may include a liquid crystal display, an organic light-emitting diode screen, a touchscreen, a cathode ray tube display, etc. As described further herein, the graphical user interface displayed by the display apparatus 22 may include multiple items related to the extracorporeal blood treatment such as, e.g., one or more fluid areas, each fluid area corresponding to a different fluid used in an extracorporeal blood treatment. Each of these fluid areas may be used by an operator to view status information corresponding to a fluid such as flow rate, an amount of fluid within a reservoir, an amount of time left before a reservoir change, etc. Further, each of these fluid areas may be used, or interacted with, by a user to change, or modify, one or more parameters associated with the fluid such as flow rate, concentration, etc.

As used herein, a "region" of a graphical user interface may be defined as a portion of the graphical user interface within which information may be displayed or functionality may be performed. Regions may exist within other regions, which may be displayed separately or simultaneously. For example, smaller regions may be located within larger regions, regions may be located side-by-side, etc. Additionally, as used herein, an "area" of a graphical user interface may be defined as a portion of the graphical user interface located with a region that is smaller than the region the area is located within.

The processing programs or routines 16 may include programs or routines for performing computational mathematics, matrix mathematics, standardization algorithms, comparison algorithms, or any other processing required to implement one or more exemplary methods and/or processes described herein. Data 18 may include, for example, fluid data, flow rates, fluid volumes, notifications, pressures, blood flow, fluid removal rates, target blood temperatures, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein, or any other data that may be necessary for carrying out the one and/or more processes or methods described herein.

In one or more embodiments, the system 10 may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The program used to implement the methods and/or processes described herein may be provided using any programmable language, e.g., a high level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the system 10 may be implemented using a computer readable storage medium, configured with a computer program, where the storage medium so configured causes the computer to operate in a specific and predefined manner to perform functions described herein. Further, in at least one embodiment, the system 10 may be described as being implemented by logic (e.g., object code) encoded in one or more non-transitory media that includes code for execution and, when executed by a processor, is operable to perform operations such as the methods, processes, and/or functionality described herein.

Likewise, the system 10 may be configured at a remote site (e.g., an application server) that allows access by one or more operator, or users, via a remote computer apparatus (e.g., via a web browser), and allows an operator to employ the functionality according to the present disclosure (e.g., an operator accesses a graphical user interface associated with one or more programs to process data).

The computing apparatus 12 may be, for example, any fixed or mobile computer system (e.g., a controller, a microcontroller, a personal computer, mini computer, etc.). The exact configuration of the computing apparatus 12 is not limiting, and essentially any device capable of providing suitable computing capabilities and control capabilities (e.g., graphics processing, control of extracorporeal blood treatment apparatus, etc.) may be used.

As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by computing apparatus 12 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

The methods and/or logic described in this disclosure, including those attributed to the systems, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, or other devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described components may be implemented together or separately as discrete but interoperable logic devices. Depiction of different features, e.g., using block diagrams, etc., is intended to highlight different functional aspects and does not necessarily imply that such features must be realized by separate hardware or software components. Rather, functionality may be performed by separate hardware or software components, or integrated within common or separate hardware or software components.

When implemented in software, the functionality ascribed to the systems, devices and methods described in this disclosure may be embodied as instructions and/or logic on a computer-readable medium such as RAM, ROM, NVRAM, EEPROM, FLASH memory, magnetic data storage media, optical data storage media, or the like. The instructions and/or logic may be executed by one or more processors to support one or more aspects of the functionality described in this disclosure.

The treatment apparatus 24 may include any apparatus used by an exemplary extracorporeal blood treatment system capable of performing extracorporeal blood treatments, such as, e.g., pumps, reservoirs, scales, treatment sets, filters, pressure sensors, etc. For example, the treatment apparatus 24 may include one or more elements, or components, of the extracorporeal blood treatment system 100 described herein with reference to FIG. 2.

The exemplary systems, and exemplary methods performed, or used, by such exemplary systems, described herein may be generally referred to as dialysis systems. The general term "dialysis" as used herein includes hemodialysis, hemofiltration, hemodiafiltration, hemoperfusion, liver dialysis, and therapeutic plasma exchange (TPE), among other similar treatment procedures. In dialysis generally, blood is taken out of the body and exposed to a treatment device to separate substances therefrom and/or to add substances thereto, and is then returned to the body. Although extracorporeal blood treatment systems capable of performing general dialysis (as defined above, including TPE) shall be described herein with reference to the exemplary extracorporeal blood treatment system of FIG. 2, other systems such as those for infusion of drugs, performance of continuous renal replacement therapy (CRRT), extracorporeal membrane oxygenation (ECMO), hemoperfusion, liver dialysis, apheresis, TPE, etc. may benefit from the systems, methods, and apparatus described herein and the present disclosure is not limited to any particular fluid processing system.

Figure 2:
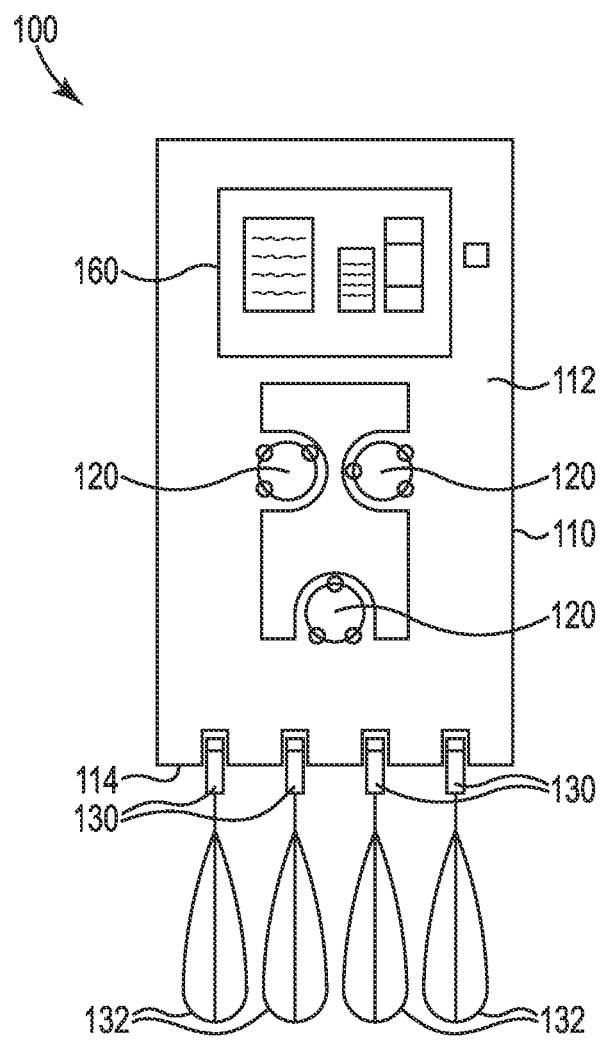
FIG. 2 is an illustration of an exemplary extracorporeal blood treatment system that may include graphical user interfaces as described herein.

Referring to FIG. 2, one illustrative embodiment of an extracorporeal blood treatment system, or apparatus, 100 is depicted. The system 100 includes a housing 110 having a front face 112. The system further includes one or more pumps 120 used to move liquids through the apparatus as part of a treatment process. Although the pumps 120 are depicted in the form of peristaltic pumps, the pumps used in the extracorporeal blood treatment system described herein may be provided in a variety of alternative forms, e.g., piston pumps, pumps for use with syringes, diaphragm pumps, etc.

The extracorporeal blood treatment system 100 also includes, in one or more embodiments, a display 160 used to convey information to an operator. The display 160 may also serve as an input device if, e.g., the display 160 is in the form of a touchscreen. Also, although the display 160 is depicted as being located in the housing 110, in one or more alternate embodiments, the display 160 may be separate from the housing 110 of the extracorporeal blood treatment system 100. For example, the display 160 may be movably (e.g., swivel, tilt, etc.) attached, or coupled, to a top end of the housing 110.

The extracorporeal blood treatment system 100 also includes reservoir scales 130, each of which is configured to hold and weigh a reservoir 132. The reservoir scales 130 are positioned below a bottom end 114 of the housing 110, at least in part because the reservoirs 132 are typically attached to and hang from the reservoir scales 130. Although the depicted embodiment of extracorporeal blood treatment system 100 includes four reservoir scales 130 and associated reservoirs 132, alternative embodiments of an extracorporeal blood treatment apparatus as described herein may include one or more reservoir scales 130 and associated reservoirs 132 such as, e.g., as few as two reservoirs scales 130 and associated reservoirs 132, four or more reservoirs scales 130 and associated reservoirs 132, etc.

In the embodiment shown, the reservoirs 132 may be in the form of, e.g., flexible polymeric bags configured to hold liquids. Reservoirs 132, however, used in connection with the exemplary extracorporeal blood treatment systems described herein may take any suitable form in which liquids can be stored and weighed by any scale or weighing apparatus (e.g., such as reservoir scales 130), e.g., bottles, tanks, cartons, syringes, jugs, etc.

As shown in FIG. 1 and as related to FIG. 2, the treatment apparatus 24 may be operatively coupled, or connected, to the computing apparatus 12. Among the treatment apparatus 24 operably coupled to the computing apparatus 12 are the pumps 120 and reservoir scales 130 as shown in FIG. 2. Each of the pumps 120 and reservoirs 132 may have a flow rate associated therewith.

The computing apparatus 12 may, in one or more embodiments, be configured to receive a weight signal from each reservoir scale 130, with the weight signal from each reservoir scale 130 being indicative of the weight of a reservoir 132 attached to the reservoir scale 130. The computing apparatus 12 may further be configured to make a determination that the reservoir 132 attached to the reservoir scale 130 from which the weight signal has been received has passed a selected weight limit at least partially based on the weight signal received from the reservoir scale 130.

Screenshots depicting exemplary graphical user interfaces for use in modifying one or more flow rates for various fluids related to extracorporeal blood treatments are depicted in FIGS. 3-15. Such exemplary graphical user interfaces may be depicted by the display apparatus 22 of the system 10 described herein with reference to FIG. 1 and/or the display 160 of the system 100 of FIG. 2. Additionally, the graphical user interfaces described herein may be depicted on a touchscreen, and in such configuration, the input apparatus would also be the touchscreen.

Figure 3:
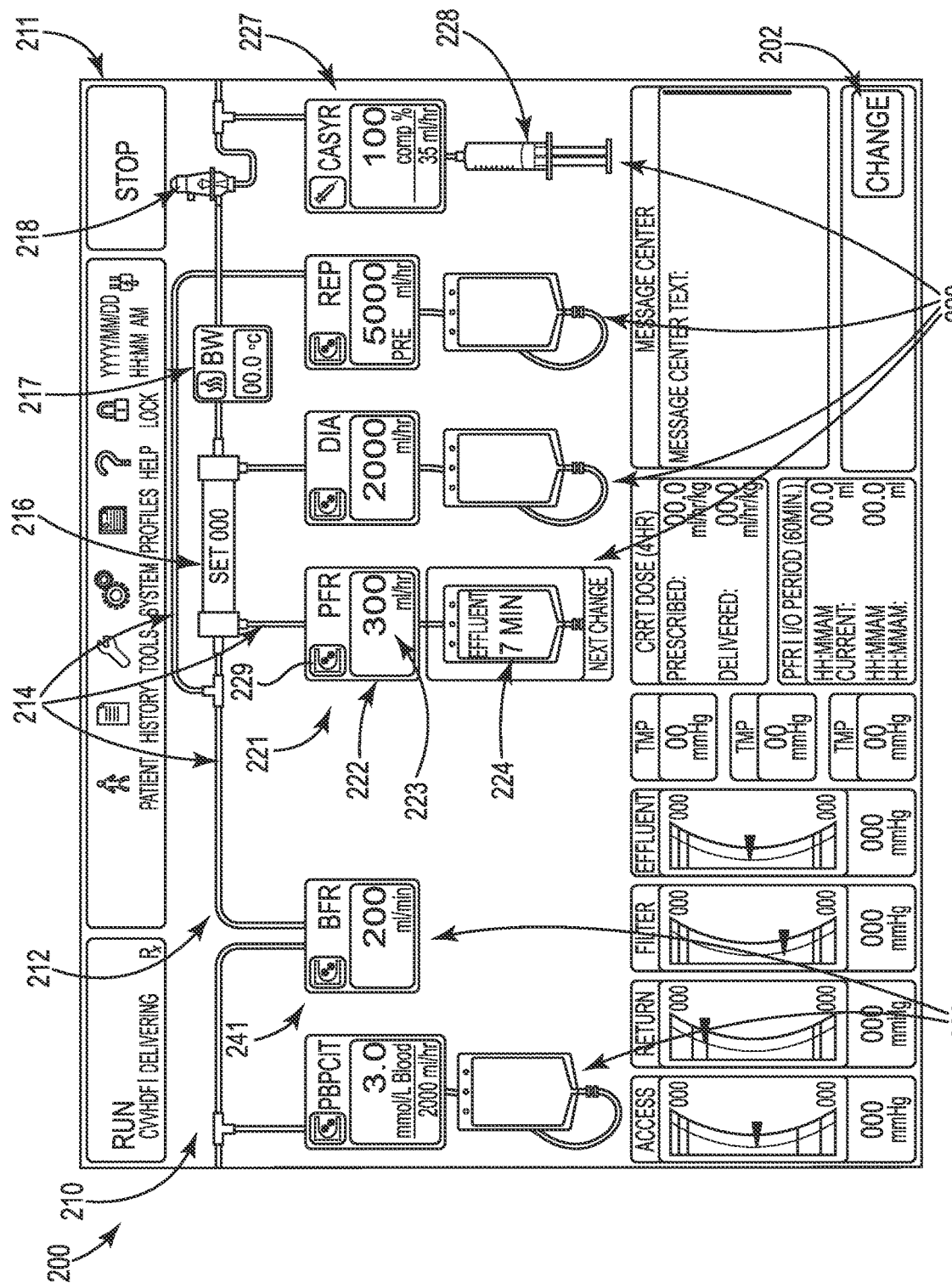
FIGS. 3-15 are screenshots of exemplary graphical user interfaces related to one or more fluid areas for use in extracorporeal blood treatment systems, for example, such as shown generally in FIGS. 1-2.

An exemplary graphical user interface 200 is depicted in FIG. 3 that may be generally used during and/or for the execution of an extracorporeal blood treatment. The graphical user interface 200 may include, among other regions, a fluids region 210. As shown, the fluids region 210 is depicted below a toolbar region 211 and extending from a left side to a right side of the graphical user interface 200. The fluids region 210 may include, or graphically depict, a plurality of fluid areas 220. Each of the fluid areas 220 may correspond to, or represent, a fluid, flow or pump rate, and/or concentration of a fluid in a physical fluid circuit used in an exemplary extracorporeal blood treatment.

Additionally, the fluids region 210 may include a fluid circuit 212 configured to diagrammatically represent the physical extracorporeal fluid circuit for an ongoing, or present extracorporeal blood treatment performed by the exemplary extracorporeal blood treatment system. The fluid circuit 212 may include one or more fluid connections 214 extending between and connecting various fluid areas 220 as well as additional items or components of the exemplary physical extracorporeal fluid circuit such as a filter set 216, blood warmer 217, and deaeration apparatus 218. Further, the fluid connections may accurately depict the physical fluid connection between the reservoirs and pumps of the extracorporeal blood treatment system. For example, the reservoir may be used to collect fluid from the patient and/or supply fluid to be used in the blood treatment process (e.g., delivered to the patient), and depending on the functionality of the reservoir, the fluid connection depicted may be different. For example, as shown in FIG. 3, the fluid connection for the PFR fluid area 221 is shown extending from the top of the reservoir element (e.g., a bag reservoir) to the pump element, which may indicate that the PFR reservoir stores and collects fluid (e.g., fluid from the patient, etc.). Further, in other fluid areas, the fluid connection may be shown extending from the bottom of the reservoir element (e.g., a bag reservoir) to the pump element, which may indicate that the reservoir stores and supplies fluid to be used in the blood treatment process.

As shown in the exemplary figures, a Continuous Veno-venous Hemodiafiltration (CVVHDF) blood treatment is being presently performed or executed by the exemplary extracorporeal blood treatment system, and thus, the plurality of fluid areas 220 and the fluid circuit 212 (e.g., including filter set 216, blood warmer 217, and deaeration apparatus 218) are configured to diagrammatically represent the exemplary physical extracorporeal fluid circuit for a CVVHDF blood treatment. The fluid areas 220 corresponding to the exemplary CVVHDF treatment depicted in the fluids region 210 are pre-blood pump citrate (PBPcit), blood flow rate (BFR), patient fluid removal (PFR), dialysate (Dia), replacement fluid (REP), and calcium fluid (CaSYR). Exemplary fluid areas may be described in PCT Patent Application No. PCT/US2014/026215 filed on Mar. 14, 2014 and entitled "Extracorporeal Blood Treatment Fluids Interface," which is incorporated herein by reference in its entirety.

Although an exemplary CVVHDF process is depicted in FIG. 3, the graphical user interface 200 may be configured for a plurality of different treatment processes such as, e.g., continuous ultrafiltration (SCUF), continuous veno-venous hemofiltration, (CVVH), continuous veno-venous hemodialysis (CVVHD), therapeutic plasma exchange (TPE), hemofiltration HP, hemoperfusion, continuous renal replacement therapy (CRRT), molecular adsorbent recirculating system (MARS), etc. For each different treatment process, the graphical user interface 200 may include a fluids region 210 that includes fluid areas 220 corresponding to the one or more different fluids or fluid configurations that are used in each different treatment process. Although, six different fluid areas 220 are depicted in the fluids region 210 as shown, it is to be understood that the fluids region 210 may display, or include, more than six fluid areas 220 or less than six fluid areas 229 depending on the treatment being executed. For example, the one or more fluid areas 220 may include fluid areas corresponding to one or more of pre blood pump, effluent, citrate, blood flow rate, patient fluid removal, dialysate, replacement fluid, anticoagulation, patient plasma loss, calcium, etc. Further, although the fluid areas 220 are described herein as being "fluid" areas corresponding to different fluids, it is to be understood that each fluid area 220 may not always describe a different "fluid," and instead, may describe the same fluid along a different portion of the extracorporeal blood treatment fluid circuit.

Each fluid area 220 may include one or more portions and/or elements to be configured to display status information related, or corresponding, to a fluid used in the extracorporeal blood treatment. Although many fluid areas 220 are similar, each fluid area 220 may be different from the next fluid area 220. For example, some fluid areas 220 may include more or less portions/elements than other fluids areas, e.g., depending of what parameters may be modified by an operator, depending on the type and amount of information to be conveyed, depending on the type of fluid, depending on where the fluid area is located within the extracorporeal blood treatment system, etc.

One or more fluid areas 220 may include a pump element and a reservoir element. The pump element of a fluid area 220 may include a graphical depiction, or icon, loosely depicting an actual pump, an acronym, or abbreviation, of the fluid, and a numerical field typically displaying the pump's flow rate. Different types of pump elements may be displayed in each fluid area 220 depending on the therapy in use, and the pump elements themselves may change depending on their state and as an operator interacts with them.

An exemplary PFR (patient fluid removal) fluid area 221 will be further described herein. It is to be understood that other fluid areas 220 may include more or less portions and/or elements than the exemplary PFR fluid area 221, and that the exemplary PFR fluid area 221 is simply one example of a fluid area 220.

The PFR fluid area 221 includes a pump element 222 and a reservoir element 224. The pump element 222 may correspond to a physical pump such as, e.g., one of the pumps 120 of the exemplary extracorporeal blood treatment system 100 described herein with respect to FIG. 2. The pump element 222 may include a pump icon, or graphical representation, 229 located in the upper left corner of the pump element 222. The pump icon 229 may be a graphical depiction of the type of pump (e.g., peristaltic pump as shown) used for the fluid, in this case PFR, corresponding to the PFR fluid area 221. In other fluid areas 220, the icons located in the pump elements, may be any other graphical depiction of a device or apparatus to be used with the fluid represented by the fluid area such as, e.g., syringe, etc. Additionally, the pump element 222 may include a text identifier portion located in the upper right corner of the pump element 222, which in this example, is "PFR."

Figure 16:
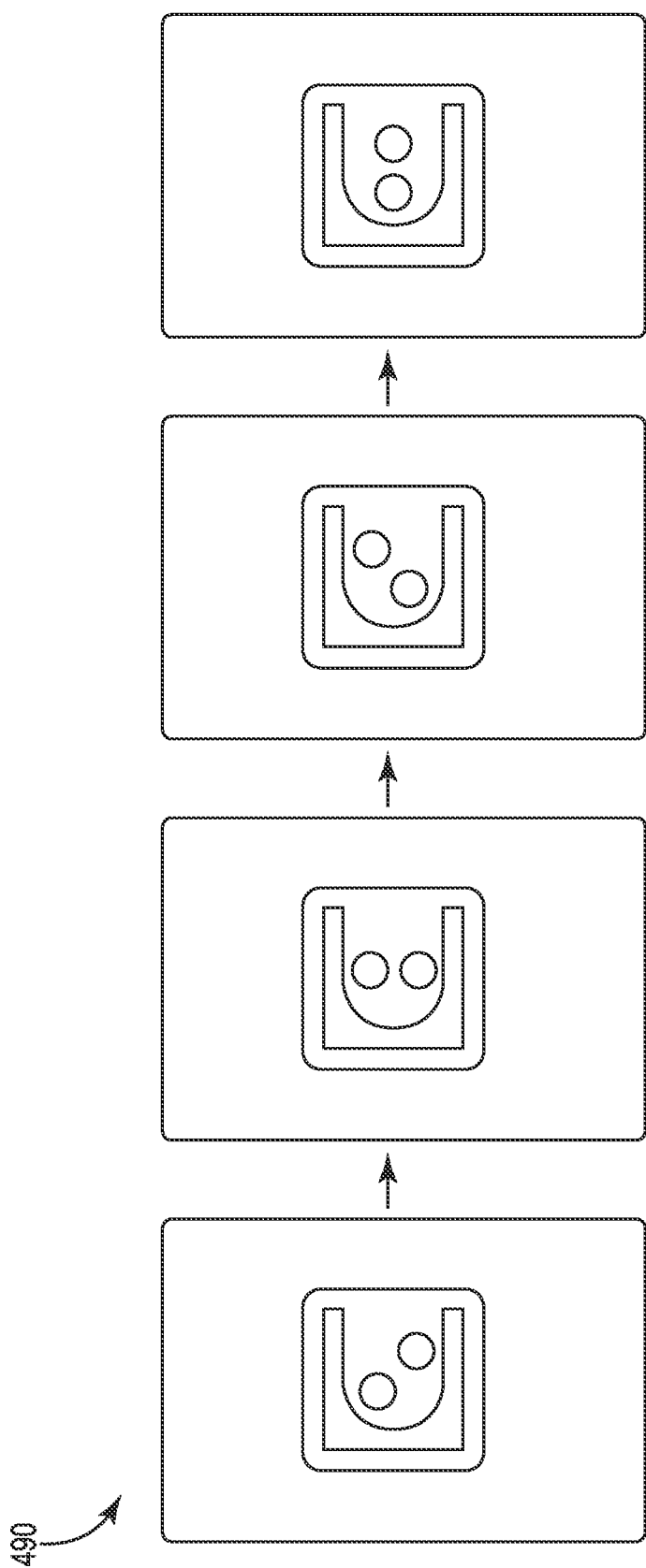
FIG. 16 depicts an animation of an exemplary pump icon.

In one or more embodiments, the pump icon 229 may be animated when, e.g., the pump associated therein is operating or running. For example, an exemplary pump icon 490 is depicted in FIG. 16 transitioning through four states of animation. More specifically, as shown, the two circles, representing two rollers or shoes of a peristaltic pump, may rotate around a central fixed point similar to the two rollers or shoes of a peristaltic pump. The icon 229 of each of the fluid areas 220 may or may not be synchronized (e.g., the circles representing the rollers being in the same phase of rotation) and/or may or may not rotate at the same rate (e.g., the rotation rate of circles representing the rollers rotating around a central, fixed point). Further, some icons 229 of fluid areas 220 may be animated while others are dormant. For example, some pumps may be running while others are not, and thus, the icons 229 of the fluid areas 220 corresponding to the running pumps may be animated while the icons 229 of the fluid areas 220 corresponding to the pumps not running may be dormant. Additionally, if the icon is a syringe, the syringe may also provide an animation, e.g., the plunger moving inwardly so as to inject fluid, when operational.

The pump element 222 further includes a flow rate 223 depicted below the pump icon 229 and the identifier portion. The flow rate 223 may alphanumerically describe, or depict, the flow, or pump, rate of the fluid corresponding to the PFR fluid area 221. Although the flow rate of the pump element 222 of the PFR fluid area is presently "300" milliliters per hour (ml/hr) as shown in FIG. 3, the flow rate may change depending on the treatment and/or phase within the treatment and may be changed or modified by an operator.

The reservoir element 224 may correspond to a physical reservoir such as, e.g., one of the reservoirs 132 of the extracorporeal blood treatment system 100 described herein with respect to FIG. 2. The reservoir element 224 may be configured to depict a fluid level representative of an amount of the fluid within a reservoir storing the fluid corresponding to the PFR fluid area 221. The fluid level may be shown in many ways. As shown, the reservoir element 224 includes a graphical depiction of a fluid (in this case, PFR) stored in a fluid bag and the fluid level representative of the amount of fluid within the reservoir is defined by the fluid graphically depicted in the fluid bag.

The reservoir element 224 may include a depiction of the physical type of reservoir being used for the fluid in the extracorporeal blood treatment system. For example, as shown, the reservoir element 224 of the PFR fluid area 221 is a graphical depiction of a fluid bag, which may correspond to the physical bag reservoir being used for PFR in the exemplary extracorporeal blood treatment system. The fluid level may correspond to the amount of fluid within the physical reservoir of the extracorporeal blood treatment system, and as such, an operator may glance at the graphical user interface 200 to determine the volume of one or more reservoirs (e.g., how empty a reservoir is, how full a reservoir is, etc.) based on the fluid levels of the fluid areas 220 without looking at the physical reservoir.

The reservoir elements of the fluid areas 220 may depict types of reservoirs other than fluid bags such as, e.g., cylinders, jugs, syringes, flasks, etc. For example, as shown in calcium fluid (CaSyr) fluid area 227 identified in FIG. 3, the reservoir element 228 depicts a syringe that includes a fluid (e.g., calcium fluid) and the plunger position (adjacent the fluid) depicts the fluid level representative of the amount of fluid within the syringe.

As described herein, an operator may want to adjust, or modify, a flow rate represented in one of the plurality of fluid areas 220 in the fluids region 210 of the exemplary graphical user interface 200. To initiate an adjustment, or modification, of a flow rate, an operator may select a region or area of the graphical user interface 200. In the example depicted herein, if an operator wanted to adjust the flow rate of any of the fluid areas 220 or physically change a reservoir represented by one of the fluid areas 220, the operator may select a change region 202 of the graphical user interface 200. In another embodiment, if an operator wanted to adjust the flow rate of a fluid area 220 or physically change a reservoir represented by one of the fluid areas 220, the operator may select any area or portion of the fluids regions 210, which will be described further herein with respect to FIGS. 10-16. In another embodiment, if an operator wanted to adjust the flow rate of a fluid area 220 or physically change a reservoir represented by one of the fluid areas 220, the operator may select the fluid area 220 to be adjusted or that may need a reservoir change.

An operator, or user, may use input apparatus 20 of the exemplary extracorporeal blood treatment system 10 described herein with reference to FIG. 1 to select one or more portions such as, e.g., regions, areas, elements, items, icons, buttons, etc. of the graphical user interface 200. For example, the input apparatus 20 may be a touch screen that corresponds to the graphical user interface 200. As used herein, when an operator "selects" a portion of the graphical user interface, it is to be understood that selecting the portion may be conducted in many different ways using many different types of input apparatus. For example, when the input apparatus is a touch screen, an operator may select a portion by "touching" the portion with their finger or using a pointing device such as a stylus. Further, for example, when the input apparatus is a mouse or similar pointing device, an operator may select a portion by locating an arrow or cursor over the desired portion "clicking" the portion. Still further, for example, when the input apparatus is a series of buttons and/or knobs, an operator may select a portion by using the buttons and/or knobs to navigate to the portion and selecting it by depressing a button and/or knob.

One or more portions (e.g., regions, areas, elements, items, icons, buttons, etc.) of the graphical user interface 200 may change when an operator is changing a parameter such as changing the flow rate of a fluid area 220, e.g., initiated by selecting the change region 202, etc. In the embodiment depicted in FIGS. 3-10, one or more portions of the fluid circuit 212 may disappear (e.g., vanish, hide, not appear, not be displayed, etc.) when adjusting a flow rate. For example, after an operator has selected the change region 202 or selected another region or area of the graphical user interface 200 to initiate a flow rate or a reservoir change, the fluid connections 214, filter set 216, and deaeration apparatus 218 of the fluid circuit 212 may disappear, vanish, be removed from the fluids region 210, etc. as shown in FIG. 4.

Additionally, the pump elements of the fluid areas 220 may also change in appearance, e.g., the pump elements may change in color, tone, etc. In other embodiments, one or more portions of the fluid circuit 212 may be graphically obscured, e.g., blurred, "greyed-out," etc. after an operator has selected the change region 202 or selected another region or area of the graphical user interface 200 to initiate a flow rate or a reservoir change. For example, one or more portions of the fluid circuit 212 may be blurred as will be described further herein with respect to FIGS. 10-15.

Figure 4:
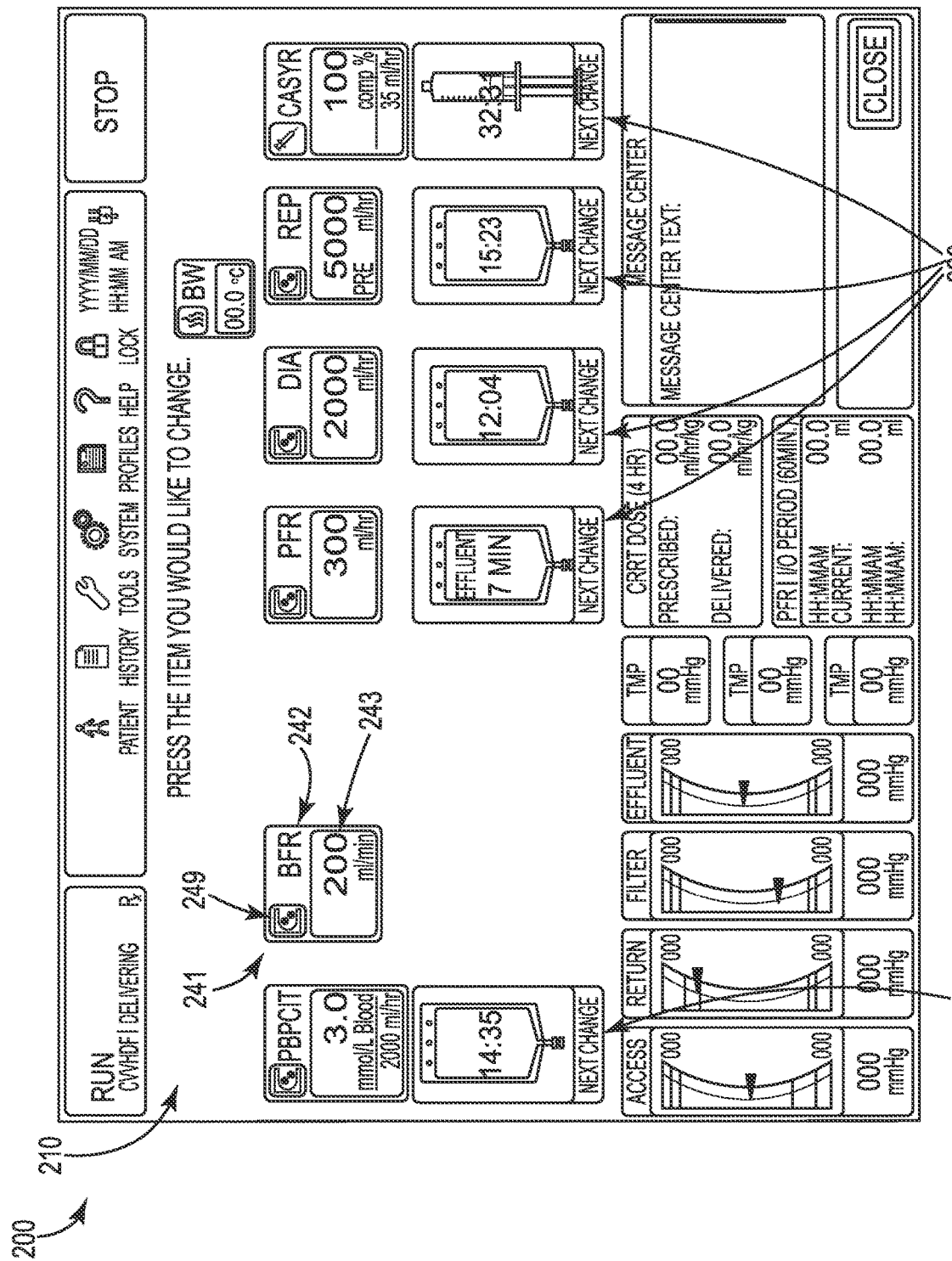
Figure 5:
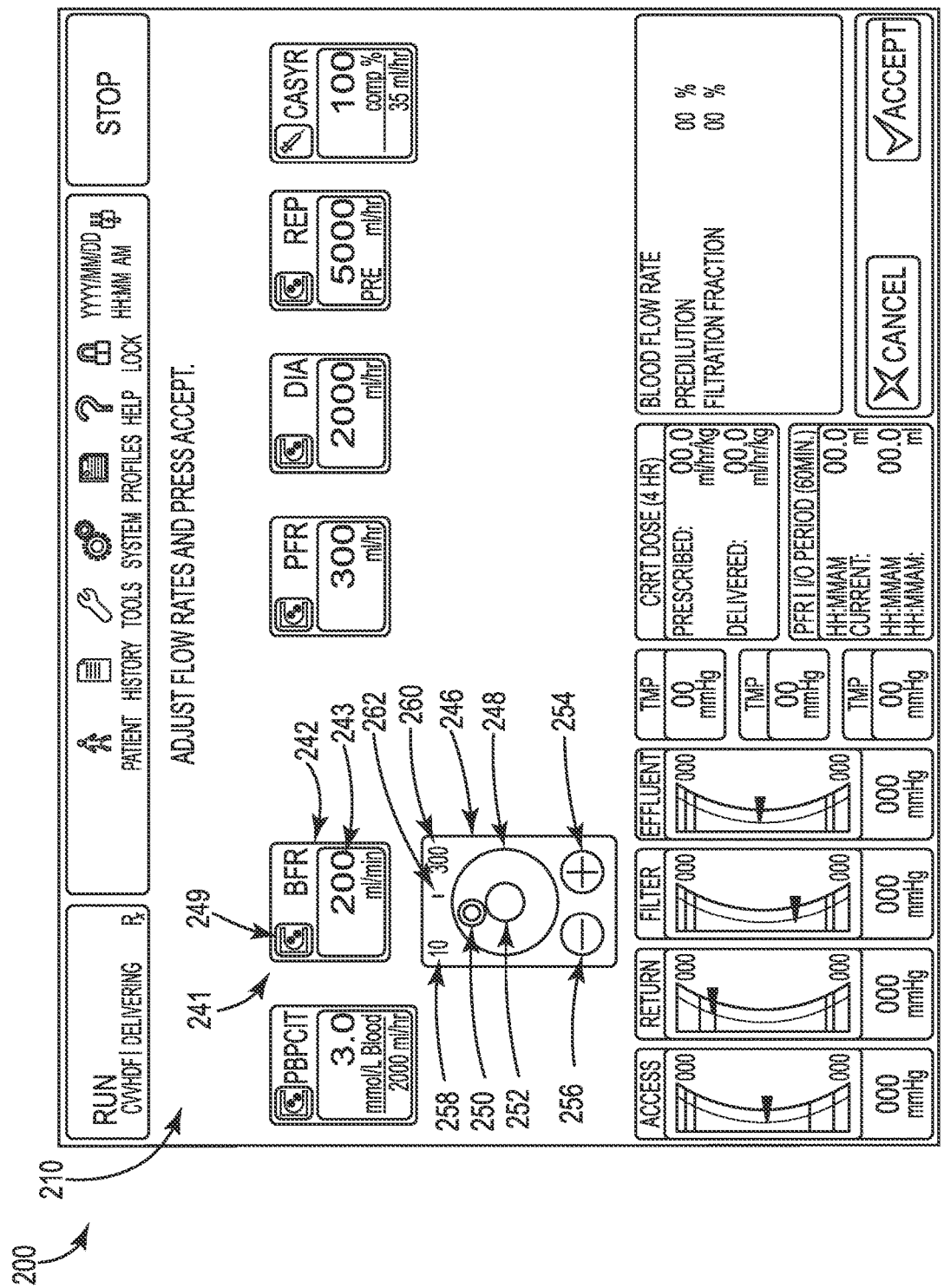

In the exemplary graphical user interface 200 of FIG. 4, if an operator wanted to adjust the flow rate 243 (presently, 200 milliliters per minute (ml/min) as depicted) of the Blood Flow Rate (BFR) fluid area 241, the operator may select the pump element 242 of the BFR fluid area 241. After the pump element 242 of the BFR fluid area 241 has been selected, a flow rate adjustment area 246 may be displayed proximate the BFR fluid area 241 as shown in FIG. 5. Although the flow rate adjustment area 246 is displayed below the pump element 242 of the BFR fluid area 241, it is to be understood that the flow rate adjustment area 246 may be located anywhere on the graphical user interface 200 (e.g., as a pop-up dialog, a pop-over area or window, etc.).

An operator may use the flow rate adjustment area 246 to adjust, or modify, the flow rate of the selected item. In this embodiment, the flow rate adjustment area 246 may include a rotary portion 248 that may be used to adjust the flow rate. For example, an operator may select an outer smaller circle 250 of the rotary portion 248 and drag, or move, the outer smaller circle 250 around a central, inner circle 252 of the rotary portion 248 similar to a crank or a dial. Moving the outer smaller circle 250 clockwise around the central inner circle 252 may increase the flow rate while moving the outer smaller circle 250 counterclockwise around the central inner circle 252 may decrease the flow rate. Although the flow rate adjustment area 246 includes a rotary portion 248 in this example, it is to be understood that the exemplary flow rate adjustment areas described herein may include any graphical user interface elements and portions to provide the functionality for flow rate adjustment. For example, a scrollable wheel may be provided by an exemplary flow rate adjustment area and will be described further herein with respect to FIGS. 13-14.

Figure 6:
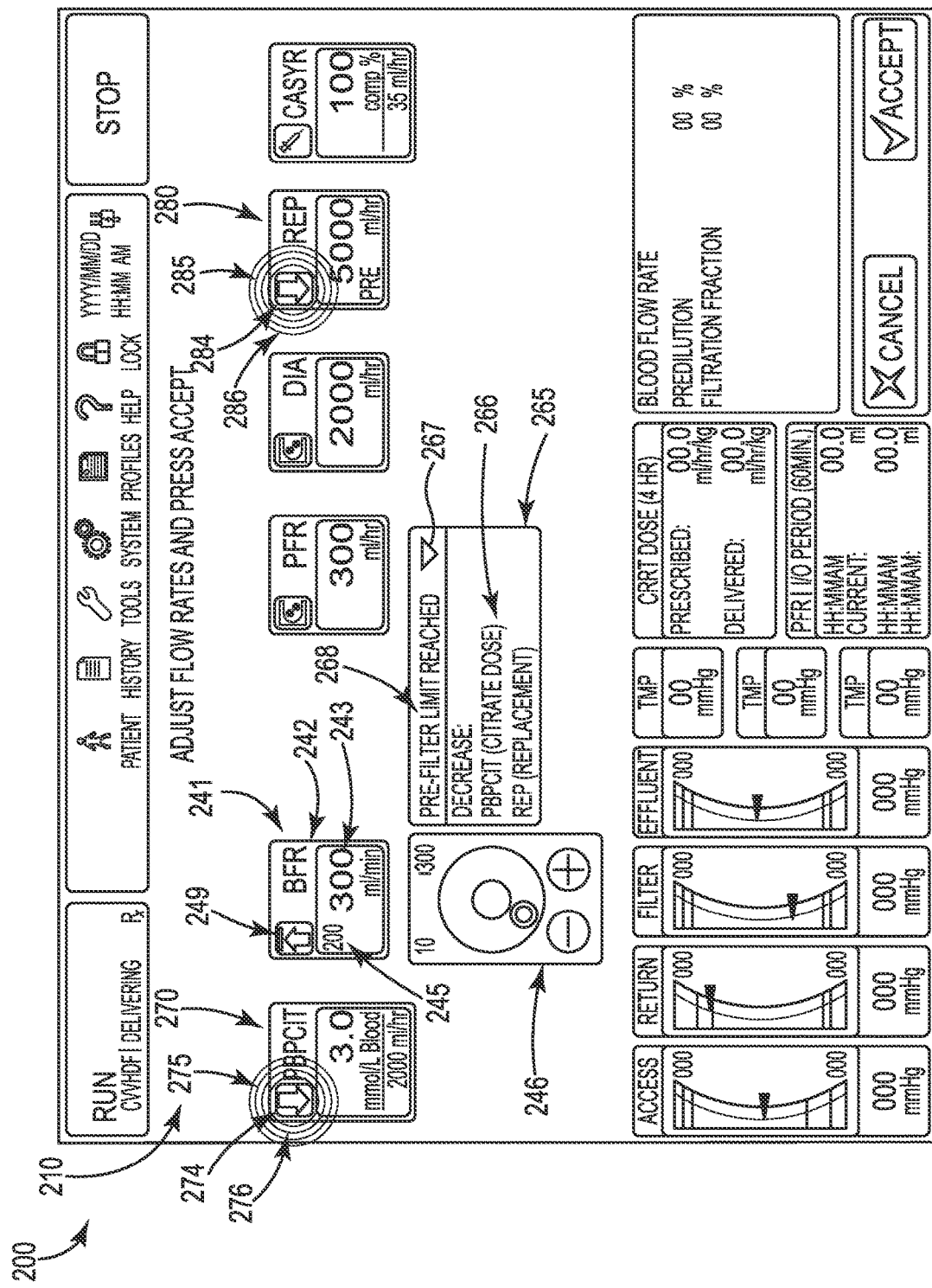

As the BFR flow rate is adjusted, a BFR flow rate 243 displayed in the pump element 242 of BFR fluid area 241 may be updated to reflect the adjusted value (e.g., the BFR flow rate 243 displayed in the pump element 242 of the BFR fluid area 241 may change while an operator is adjusting the BFR flow rate using the flow rate adjustment area 246). Further, as shown in FIG. 6, while a flow rate is being modified, the previous flow rate 245 (e.g., the flow rate prior to any modification or adjustment) may also be indicated within the pump element 242. As shown, the previous flow rate 245 is indicated in smaller text next to the flow rate 243 within the pump element 242.

Additionally, as shown in FIG. 5, the flow rate adjustment area 246 may include a plus button 254 and a minus button 256 that may be selected by an operator to increment and decrement, respectively, the flow rate 243. Further, a range of available flow rates may be indicated by a lower limit, or a lower range number, 258 (10 ml/min as shown) located in the upper left of the flow rate adjustment area 246 and an upper limit, or an upper range number, 260 (300 ml/min as shown) located in the upper right of the flow rate adjustment area 246. Further, the current flow rate (e.g., the flow rate being adjusted) may be indicated within the range by line 262 located (e.g., proportionally located based on the selected flow rate) between the upper and lower range numbers 258, 260.

When an operator adjusts a flow rate of a particular fluid area 220 (e.g., using an adjustment area 246) to a limit such as the lower limit 258 or the upper limit 260, one or more adjustment notifications may be depicted, or displayed, proximate the particular fluid area 220 and/or one or more additional fluid areas 220 that may be adjusted to modify the limit of the particular fluid area 220. For example, as shown in FIG. 6, an operator has adjusted the BFR flow rate 243 to 300 ml/min, which as shown in the flow rate adjustment area 246, is the upper limit 260 for BFR. As a result, an exemplary notification 275 has been displayed proximate the pre-blood pump citrate (PBPcit) fluid area 270 to indicate that the flow rate for PBPcit may be decreased to increase the upper limit 260 of the BFR fluid area 241 and an exemplary notification 285 has been displayed proximate the Rep fluid area 280 to indicate that the flow rate for replacement fluid (Rep) may be decreased to increase the upper limit 260 of the BFR fluid area 241.

The notifications 275, 285 include an icon indicating a decrease in flow rate for each of PBPcit and Rep, respectfully. Specifically, the icons 274, 284, which previously were icons depicting peristaltic pumps as shown in FIG. 5, have changed to arrows pointing downwardly, e.g., to indicate that a decrease in the flow rate of each of these fluid areas 270, 280 is needed to adjust the upper limit 260 of the BFR fluid area 241. Additionally, each of the icons 274, 284 may also flash, pulse, or be animated with another graphical animation as represented by the concentric rings 276, 286.

One or more elements or portions of, or proximate to, the BFR fluid area 241 may change as well when a limit such as the upper limit 260 is met. For example, the icon 249, which previously was an icon depicting a peristaltic pump as shown in FIG. 5, of the pump element 242 of the BFR fluid area 241 has changed to an arrow pointing upwardly, e.g., to indicate that a decrease in the PBPcit and/or Rep fluid areas 270, 280 will result in an increased upper limit 260.

Additionally, an adjustment information area 265 may be depicted proximate the BFR fluid area 241. The adjustment information area 265 may be configured to provide information relevant to the limit being met and one or more actions that may be taken to modify the met limit. For example, the adjustment information area 265 may include a title portion 268 describing the limit that has been met (e.g., a description of limit). As shown, the title portion 268 recites "Pre-filter Limit Reached," which may provide additional indication of what limit has been met or reached when adjusting BFR flow rate 243 using the adjustment area 246. The adjustment information areas 265 may further include an information block 266 depicting text that may include one or more instructions. The information block 266 may be described as providing a description of one or more actions that may be required to be performed on one or more other fluid areas 220 to modify the limit. As shown, the information block 266 instructs an operator to decrease the PBPcit (pre-blood pump citrate) flow rate and/or Rep (Replacement Fluid) flow rate so as to increase the upper limit 260 for BFR flow rate 243.

An operator may require additional information or additional instruction regarding the limit and/or how to adjust the limit. To provide additional information, the adjustment information area 265 may include an additional information element 267 that upon selection by an operator may provide additional information including one or more of a description of the limit, a description of one or more other fluids areas, and a description of one or more actions to be performed using one or more other fluid areas 220 to adjust or modify the limit. For example, additional information 269 is shown in the adjustment information area 265 of FIG. 7 that may be depicted, or shown, after an operator has selected the additional information element 267. Conversely, if an operator would like to revert back to the information shown in the information area 265 of FIG. 6, an operator may select the additional information element 267 again.

In one or more embodiments, if a limit may be adjusted (e.g., increased in the case of an upper limit or decreased in the case of a lower limit) for a selected fluid area 220 by adjustment of a single flow rate of another fluid area 220, then the exemplary systems and methods may provide automatic adjustment of the single flow rate of the another fluid area. In other words, the limit of a first flow rate may be dependent on only one more other flow rate—a second flow rate. In this situation, the second flow rate may be automatically adjusted when the limit of the first flow rate is met. For example, the exemplary methods and systems may allow an operator adjust the limit of the first flow rate when the limit is met, e.g., through one or more various additional graphics and/or dialogs, after a single warning and confirmation that adjusting the limit will adjust the flow rate of another identified fluid area, etc., which will thereby adjust the second flow rate corresponding to the limit adjustment. Further, in one or more embodiments, one or more flow rates of other fluid areas 220 may automatically adjust without user intervention based on the limits and/or flow rates being adjusted in a selected fluid area. When a flow rate of a fluid area 220 is automatically adjusted, the fluid area 220 may be graphically changed or highlighted to indicate that the fluid area has been automatically adjusted. For example, if the PBPcit fluid area 270 is adjusted, the CaSyr fluid area may be automatically adjusted to correspond to the PBPcit adjustment, and after or during, adjustment, the CaSyr fluid area may graphically changed or a graphical indication may be provided to indicate that it was been automatically adjusted (e.g., highlighted, whitened, etc.).

Figure 8:
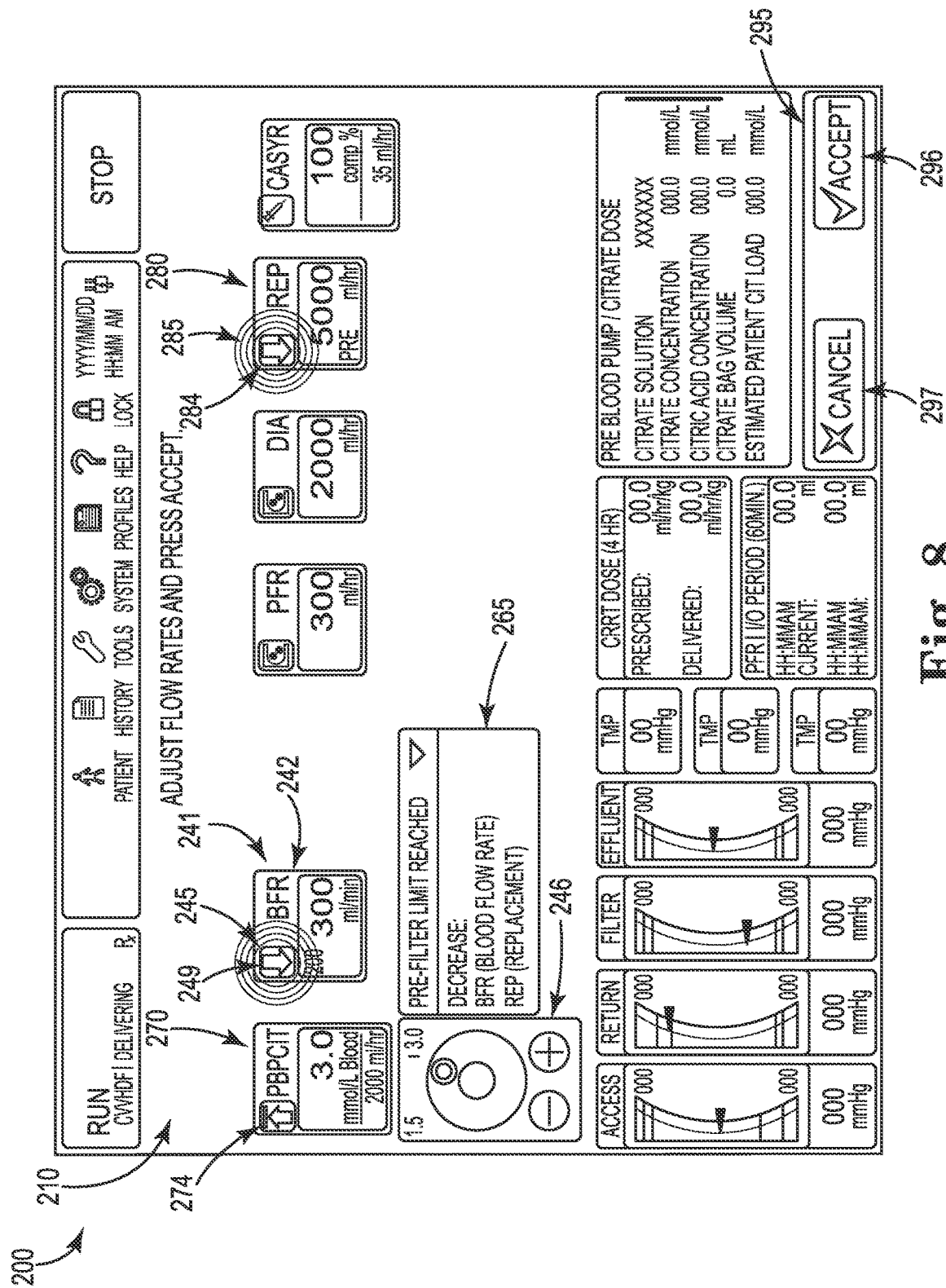

Based upon, e.g., the information provided by the notifications 275, 285 and adjustment information area 265, an operator may decide to adjust one or more flow rates of the indicated fluid areas 270, 280 to change the limit as shown in FIG. 8. As shown, an operator has selected the pre-blood pump citrate (PBPCit) fluid area 270 to adjust the flow rate thereof. Similar to when the BFR fluid area 241 was selected, adjustment notifications 245, 285 may be depicted since the PBPcit flow rate is at its upper limit (e.g., because the BFR flow rate is dependent on the PBPcit flow rate and has been adjusted to its limit). In this example, the adjustment notifications 245, 285 are depicted proximate the BFR fluid area 241 and Rep fluid area 280, respectively, since, e.g., the flow rates for BFR and Rep are dependent on the PBPcit flow rate. Further, an adjustment information area 265 may also be depicted proximate the PBPCit fluid area 270 providing information with respect to the met limit of PBPcit.

Figure 9:
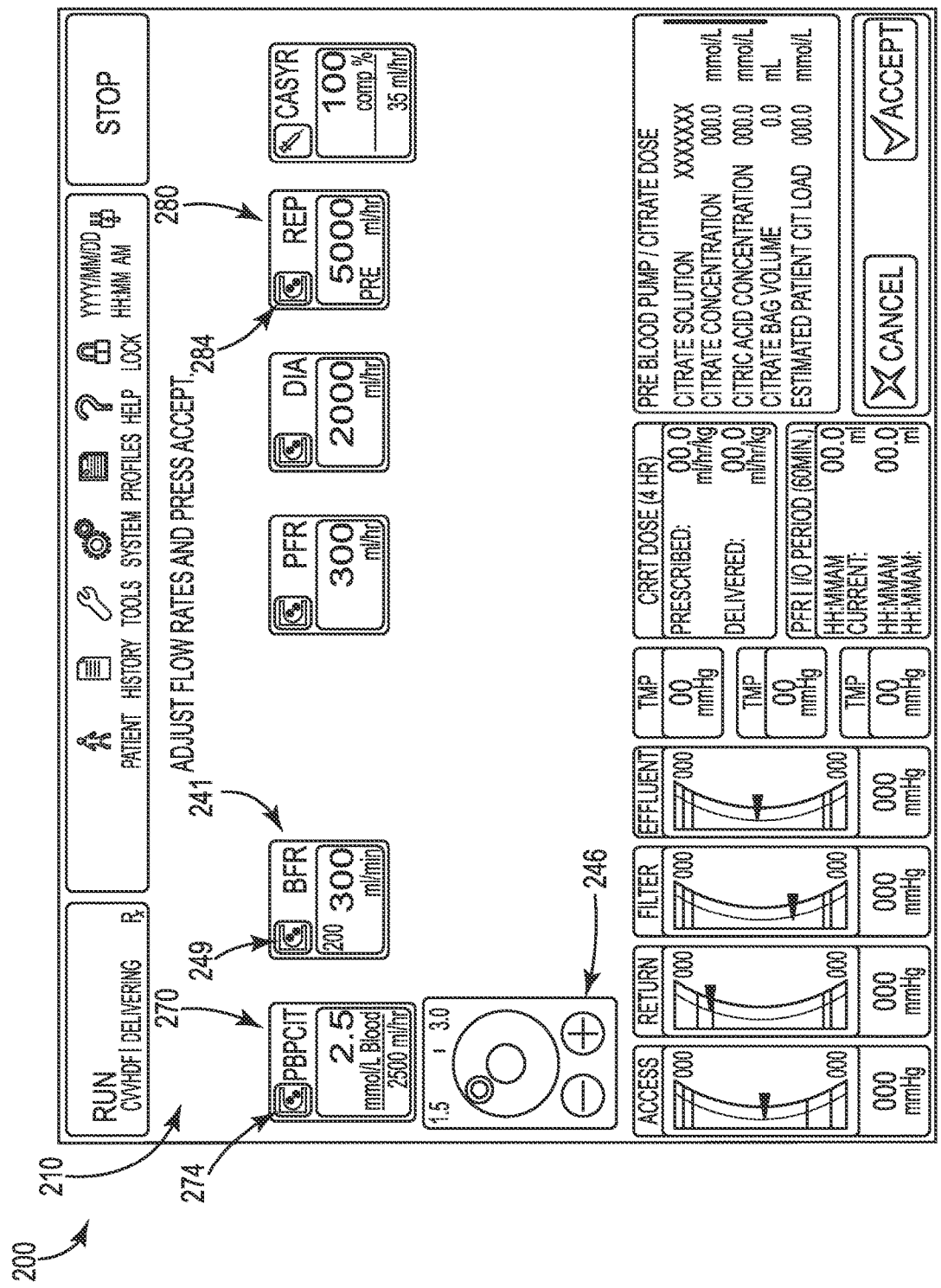
Figure 10:
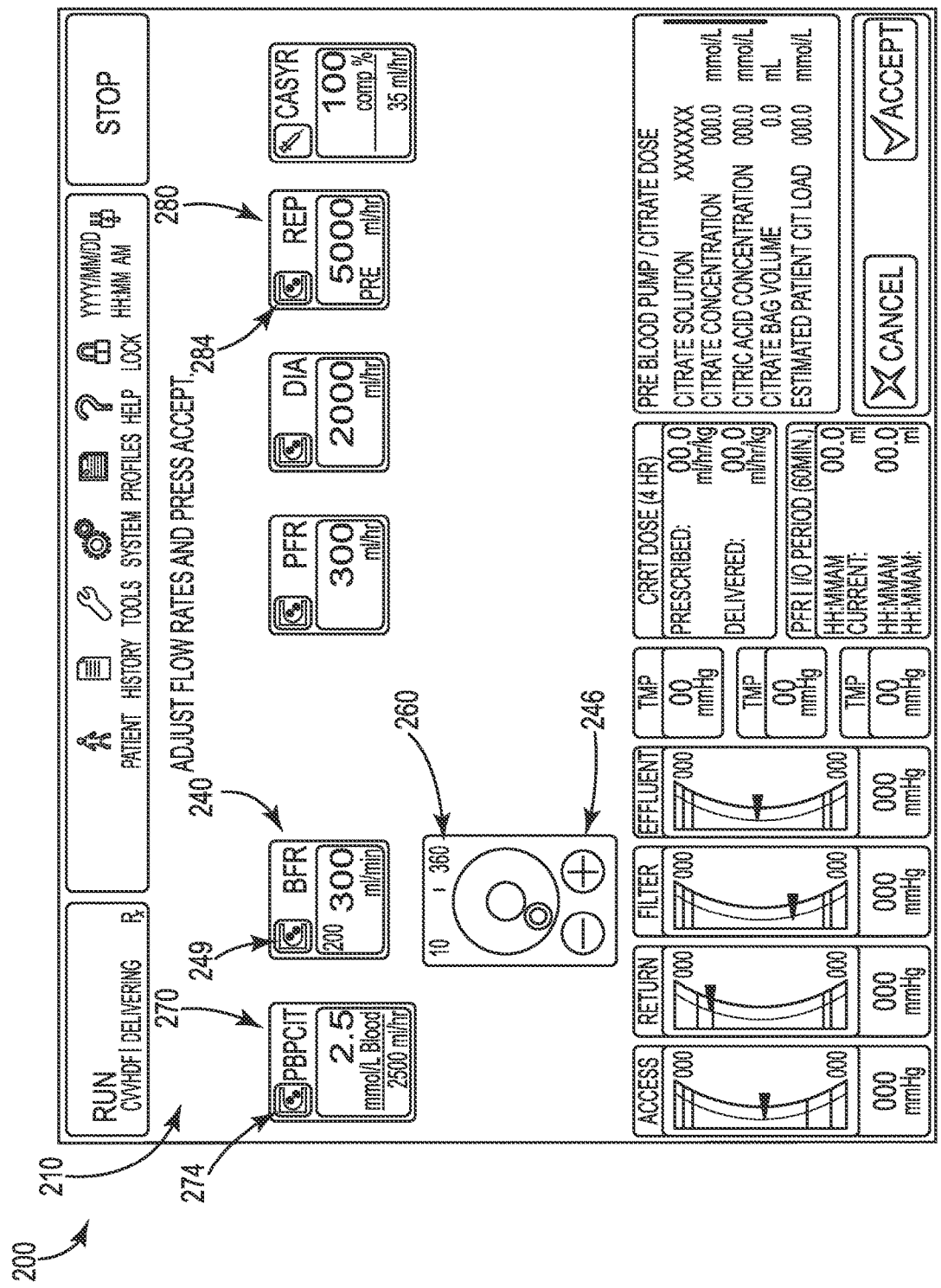

As shown, the flow rate of PBPCit, which is 3.0 mmol/L Blood, has reached its upper limit. As indicated, in the exemplary graphical user interface 200 of FIGS. 6-8, the PBPCit flow rate must be decreased to increase the upper limit of BFR flow rate, which, in this example, is the intended purpose. Thus, an operator may adjust the PBPcit flow rate using an adjustment area 246 to, e.g., 2.5 mmol/L Blood as shown in FIG. 9. After adjustment as shown, the adjustment notifications 245, 285 and/or adjustment information area 265 may be disappear (e.g., vanish, be removed, etc.) from the graphical user interface 200 because, e.g., the PBPcit flow rate is not at its upper limit anymore. Further, as shown in FIG. 10, an operator may switch back to adjusting the BFR by selecting the BFR fluid area 241, and as shown, the upper limit 260 of the BFR fluid area 241 has increased to 360 ml/min.

After an operator has adjusted the flow rates of the fluid areas 220 as intended, the operator may initiate the exemplary system to implement such adjusted flow rates by selecting an "Accept" area 296 of a confirmation region 295 of the graphical user interface 200 as shown in FIG. 8. Conversely, if the operator does not want to implement the adjusted flow rates, the operator may select a "Cancel" area, or button, 297 of the confirmation region 295, which, e.g., would revert the flow rates of the fluid areas 220 back to what they were prior to adjustment.

As described herein, when one or more flow rates are being adjusted in a fluids region of the exemplary graphical user interface, one or more portions (e.g., regions, areas, elements, icons, graphics, etc.) within the fluids region may disappear or be removed from the graphical user interfaces. In other embodiments, when one or more flow rates are being adjusted in a fluids region of the exemplary graphical user interfaces, one or more portions of the graphical user interface within the fluids region such as, e.g., one or more elements of a fluid circuit, may be graphically modified (e.g., emphasized, etc.) as opposed to vanishing, being removed, etc.

Figure 11:
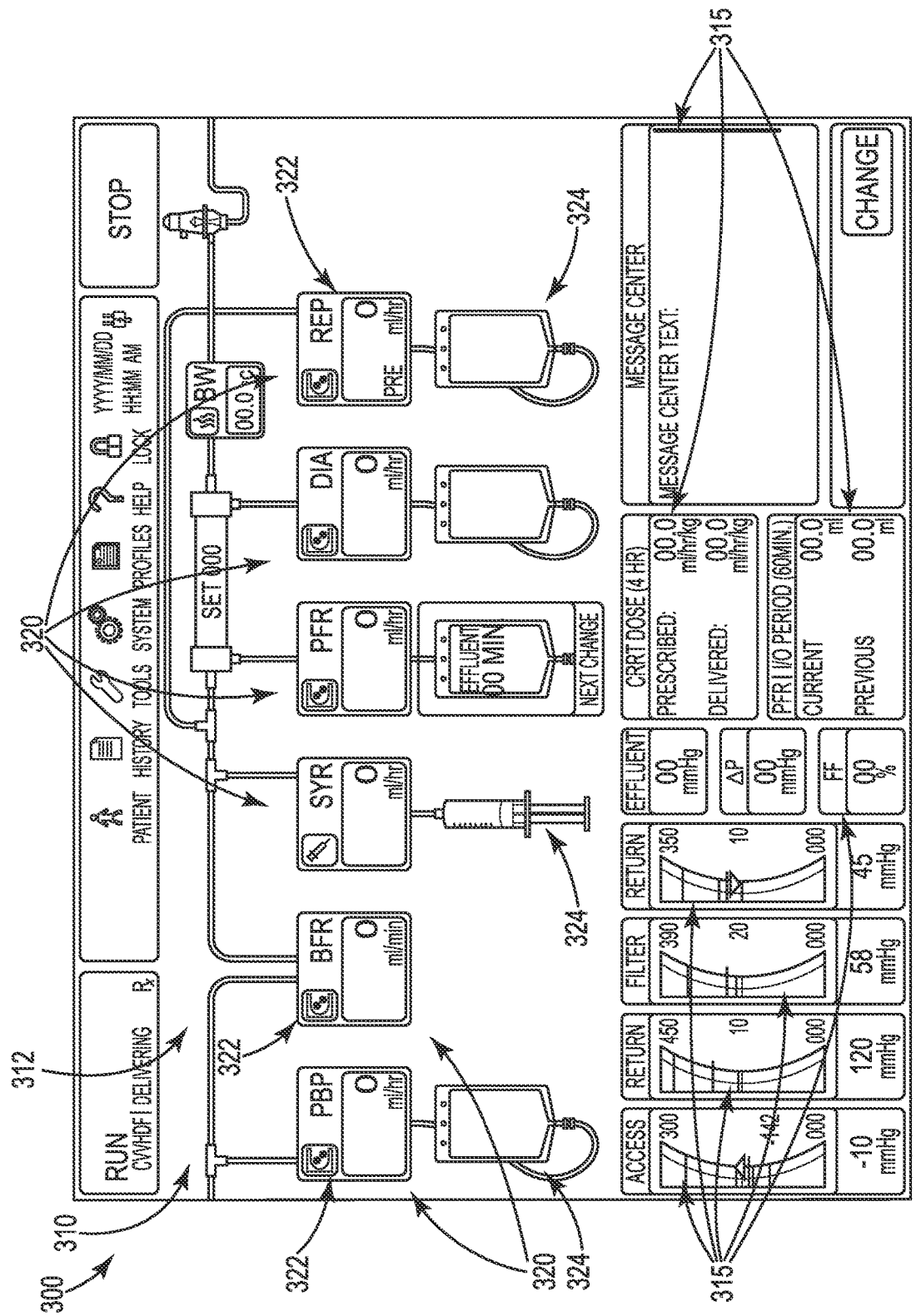
Figure 12:
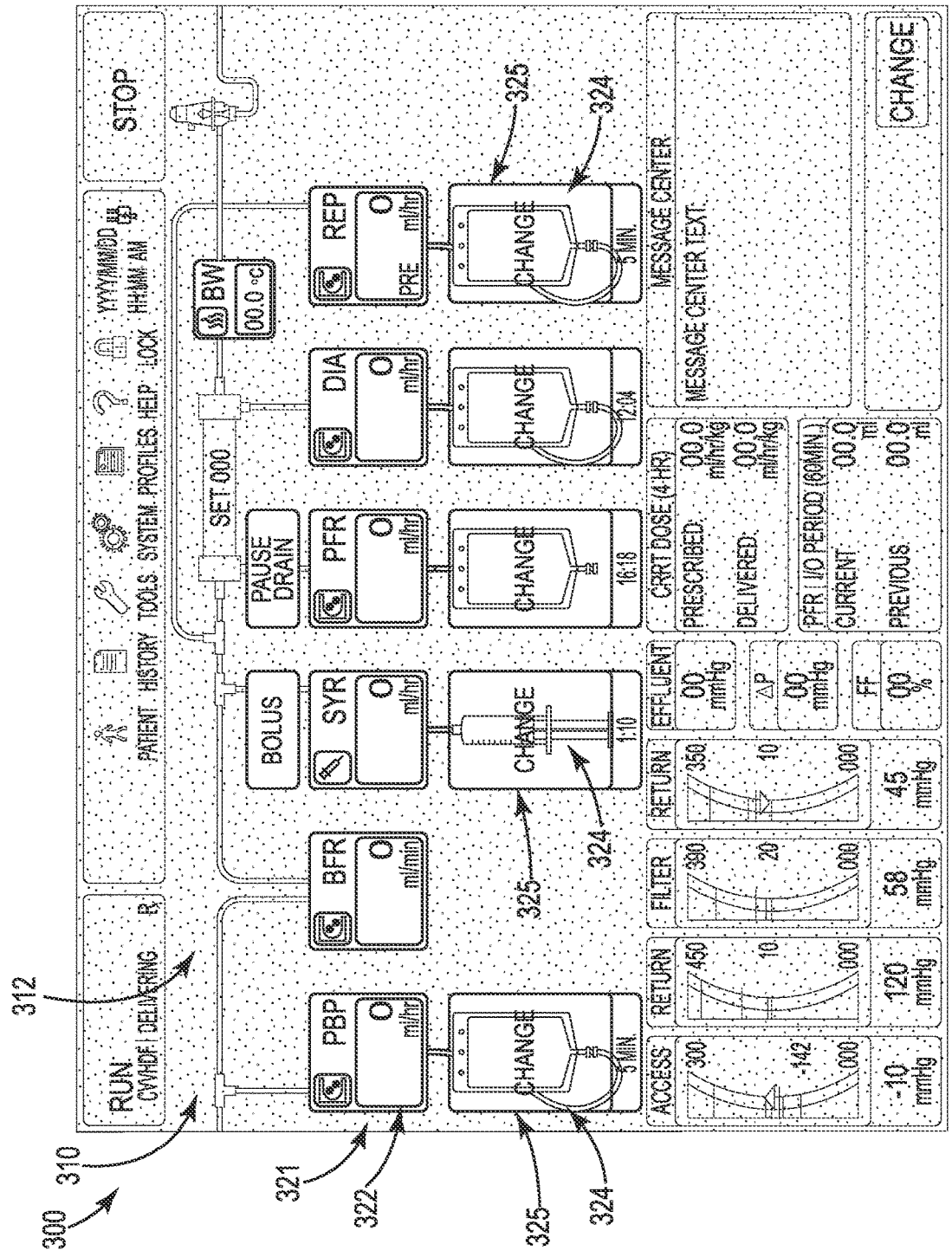

Another exemplary graphical user interface 300 that includes a fluids region 310 is depicted in FIGS. 11-15. In this graphical user interface 300, one or more portions of a fluid circuit 312 and reservoir elements of the fluid areas 320 of the fluids region 310 may be graphically modified when adjusting a flow rate and/or when initiating a reservoir change. For example, if an operator would like to adjust a flow rate or change a reservoir using the graphical user interface 300 of FIG. 11, an operator may select any location within the fluids region 310 and the graphical user interface 300 may graphically change or transition into that of FIG. 12. As shown in FIG. 12, the fluid circuit 312, reservoir elements 324, and one or more additional regions 315 of the graphical use interface 300 have been graphically modified, e.g., to indicate that a flow rate adjustment or reservoir change may occur. As shown, the graphical modification of the fluid circuit 312, reservoir elements 324, and one or more additional regions 315 may be described as an obscuring of the fluid circuit 312, reservoir elements 324, and one or more additional regions 315. For example, the fluid circuit 312, reservoir elements 324, and one or more additional regions 315 may be blurred and/or darkened (e.g., low lighted). In other embodiments, the fluid circuit 312, reservoir elements 324, and one or more additional regions 315 may be pixelated, low lighted (e.g., provided with lower light or brightness than others), and/or modified with any other graphical effect.

Additionally, the graphical modification from FIG. 11 to FIG. 12 may be described as emphasizing of the pump elements 322 and/or change reservoir elements 325 and/or deemphasizing the fluid circuit 312, reservoir elements 324, and one or more additional regions 315. For example, the pump elements 322 and change reservoir elements 325 may be brightened and/or may include more "attention grabbing" color while the fluid circuit 312, reservoir elements 324, and one or more additional regions 315 may be darkened and/or may include less "attention grabbing" color. Further, any other type of "attention grabbing" graphical user element, animation, or depiction may be used to distinguish between the pump elements 322 and/or change reservoir elements 325 from the fluid circuit 312, reservoir elements 324, and one or more additional regions 315. For example, a border may be displayed around the pump elements 322 and/or change reservoir elements 325 and everything within the border may be graphically emphasized while everything outside of the border may be graphically deemphasized.

When one or more portions of the graphical user interface 300 are de-emphasized (e.g., low lighted), they may also be rendered non-functional or inoperable. For example, the de-emphasized portions may no longer be able to be interacted with by an operator (e.g., to change a flow rate, etc.).

Figure 13:
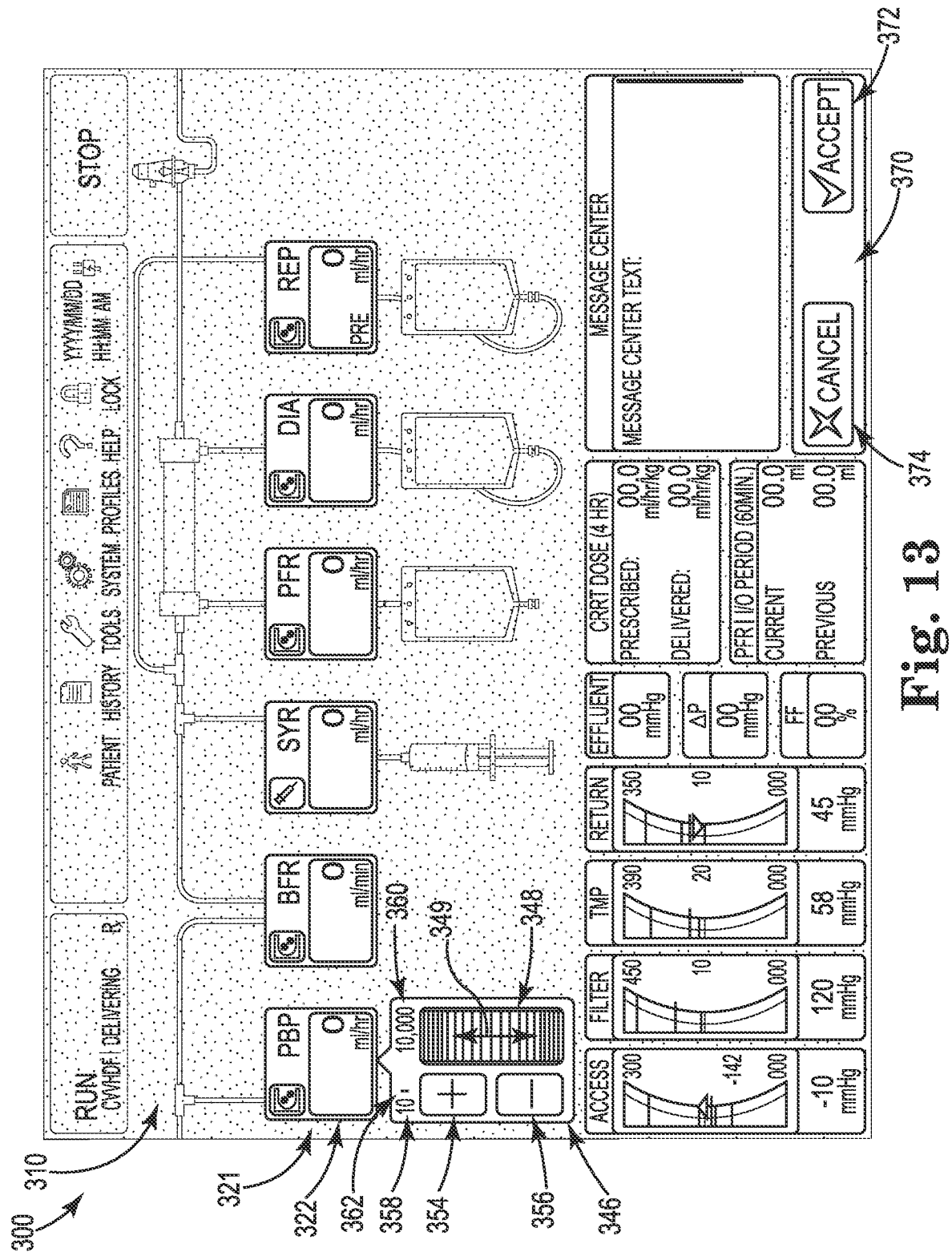
Figure 14:
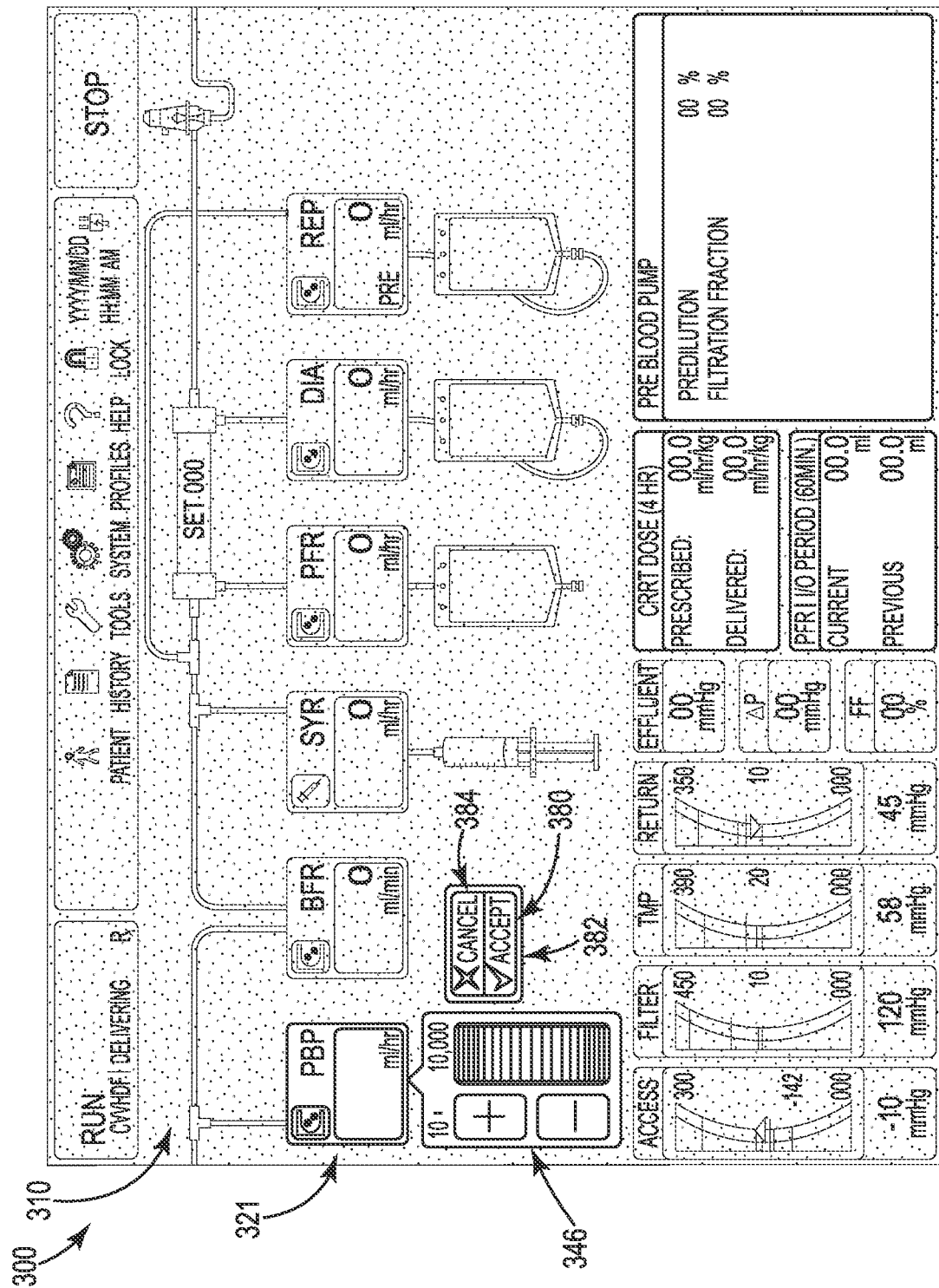

Further, a particular fluid area 320 may be selected for adjustment by selecting pump element 322 of the particular fluid area 320. When a fluid area 320 has been selected for adjustment, the change reservoir elements 325 may be removed from the graphical user interface 300 as shown in FIGS. 13-14 (e.g., which may further expose the graphically de-emphasized reservoir elements 324).

Figure 7:
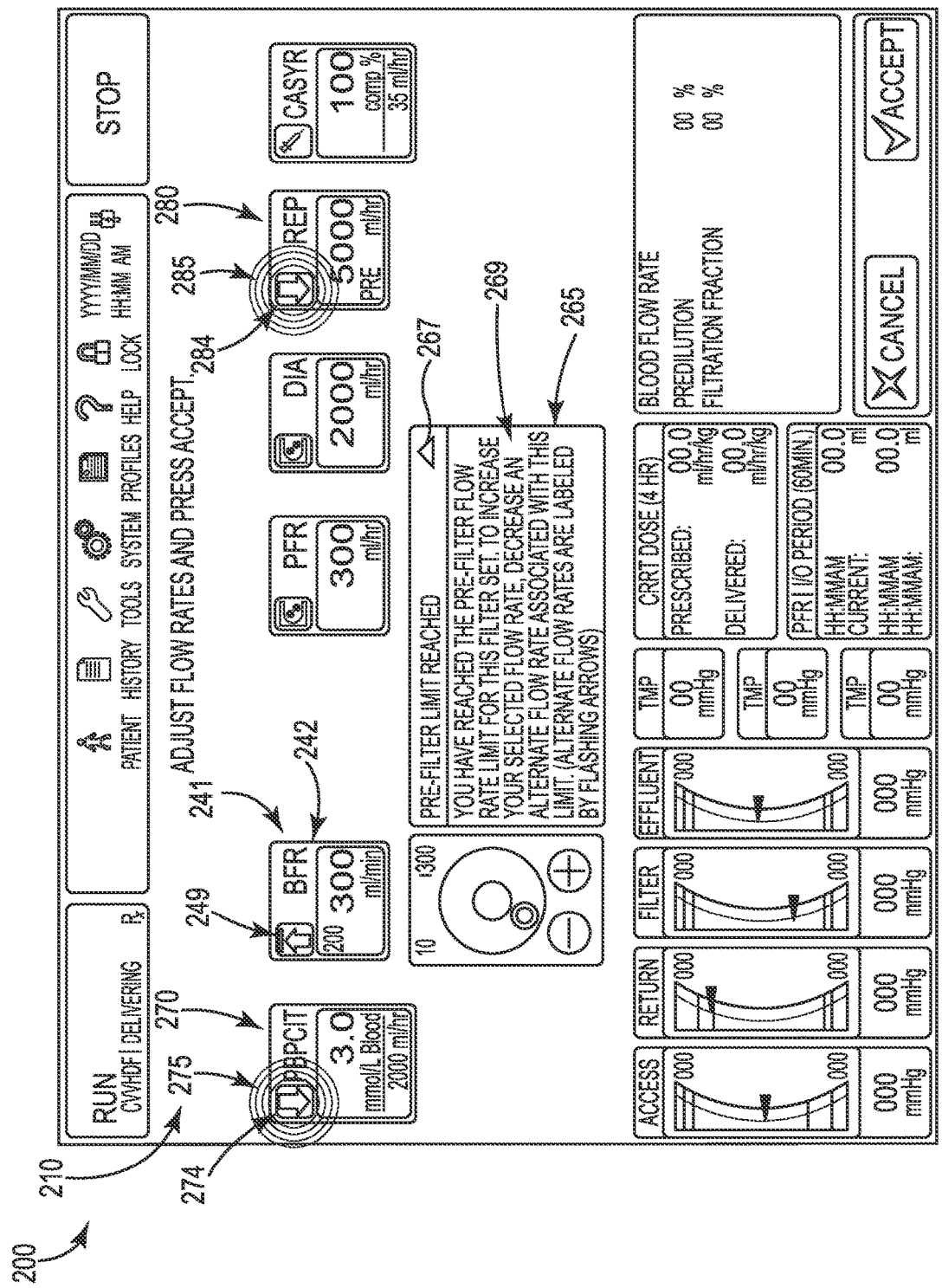

As described herein, different flow rate adjustment areas may be used by the exemplary methods and systems. A flow rate adjustment area that is different from the flow rate adjustment area 246 described herein with respect to FIGS. 6-7 is shown in FIGS. 13-14. For example, if an operator would like to adjust the flow rate of PBP, and thus, selected the pump element 322 of the PBP fluid area 321, a flow rate adjustment area 346 may be depicted proximate the PBP fluid area 321 as shown in FIG. 13. The flow rate adjustment area 346 may include lower and upper limits 358, 360, line 362, and plus and minus elements 354, 356 that may be similar to lower and upper limits, 258, 260, line 262, and plus and minus elements 254, 256 of the flow rate adjustment area 246 described herein with respect to FIGS. 6-7. The flow rate adjustment area 346 may include a scrollable wheel 348 that may be scrolled (e.g., swiped by a finger of an operator) up or down (represented by arrow 349) to adjust the flow rate of PBP.

After the flow rate has been adjusted, an operator may select an accept element 372 within the confirmation region 370 of the graphical user interface 300. After selecting the accept element 372, the graphical user interface 300 may change back to as shown in FIG. 11 or FIG. 12 (e.g., with an adjusted flow value). Further, if an operator decides to cancel the flow rate adjustment, the operator may selected the cancel element 374 within the confirmation region 370 of the graphical user interface 300, which may revert the graphical user interface 300 back to as shown in FIG. 11 or FIG. 12.

In another embodiment, a confirmation region may be depicted, or displayed, proximate the fluid area 320 being modified. For example, as shown in FIG. 14, a confirmation region 380 including accept and cancel elements 382, 384 is depicted proximate the fluid area 321 and may provide the same functionality as the confirmation region 370. In other embodiments, the confirmation region 370 may always be displayed when the flow rate adjustment area 246 is displayed.

Additionally, as shown in FIG. 14, the PBP fluid area 321 is graphically emphasized (e.g., brightened, increased brightness, highlighted, etc.) while the remainder of the fluids region 310 and/or other portions of the graphical user interface 300 (e.g., fluid circuit 312, other regions 315) are deemphasized (e.g., darkened, low lighted, decreased brightness, blurred, pixelated, etc.). This graphical modification of the portions of the graphical user interface 300 may occur directly after a user has selected a fluid area 320 for adjustment from the graphical user interface 300 shown in FIG. 11. For example, if an operator would like to adjust the PBP flow rate, the operator may select (e.g., touch) the pump element of the PBP fluid area 321 in FIG. 11 and the graphical user interface 300 may transition, or change, to that of FIG. 14, where all but the pump element of the PBP fluid area 321 and adjustment area 346 are graphically de-emphasized. Further, it may be described that graphical user interface 300 is configured to allow an operator to select a selected fluid area 321 of the plurality of fluid areas 320 to initiate an action (e.g., flow rate change, reservoir change, etc.) associated with the selected fluid area 321. The other, non-selected fluid areas 320 may be graphically modified (e.g., de-emphasized) and rendered non-functional once a fluid area such as PBP fluid area 321 has been selected. A fluid area 320 is rendered non-functional or inoperable when it is no longer able to be interacted with by an operator (e.g., to change a flow rate, etc.).

From the graphical user interface 300 depicted in FIG. 12, an operator may choose to adjust a flow rate of one of the one or more fluid areas 320 or change a reservoir for one of the one or more fluid areas 320. If an operator chooses to change a reservoir, an operator may select a reservoir element 324 of the particular fluid area 320 corresponding to reservoir to be changed. For example, if an operator would like to change the PBP reservoir, the operator may select the reservoir element 324 of the PBP fluid area 321 in FIG. 12.

Figure 15:
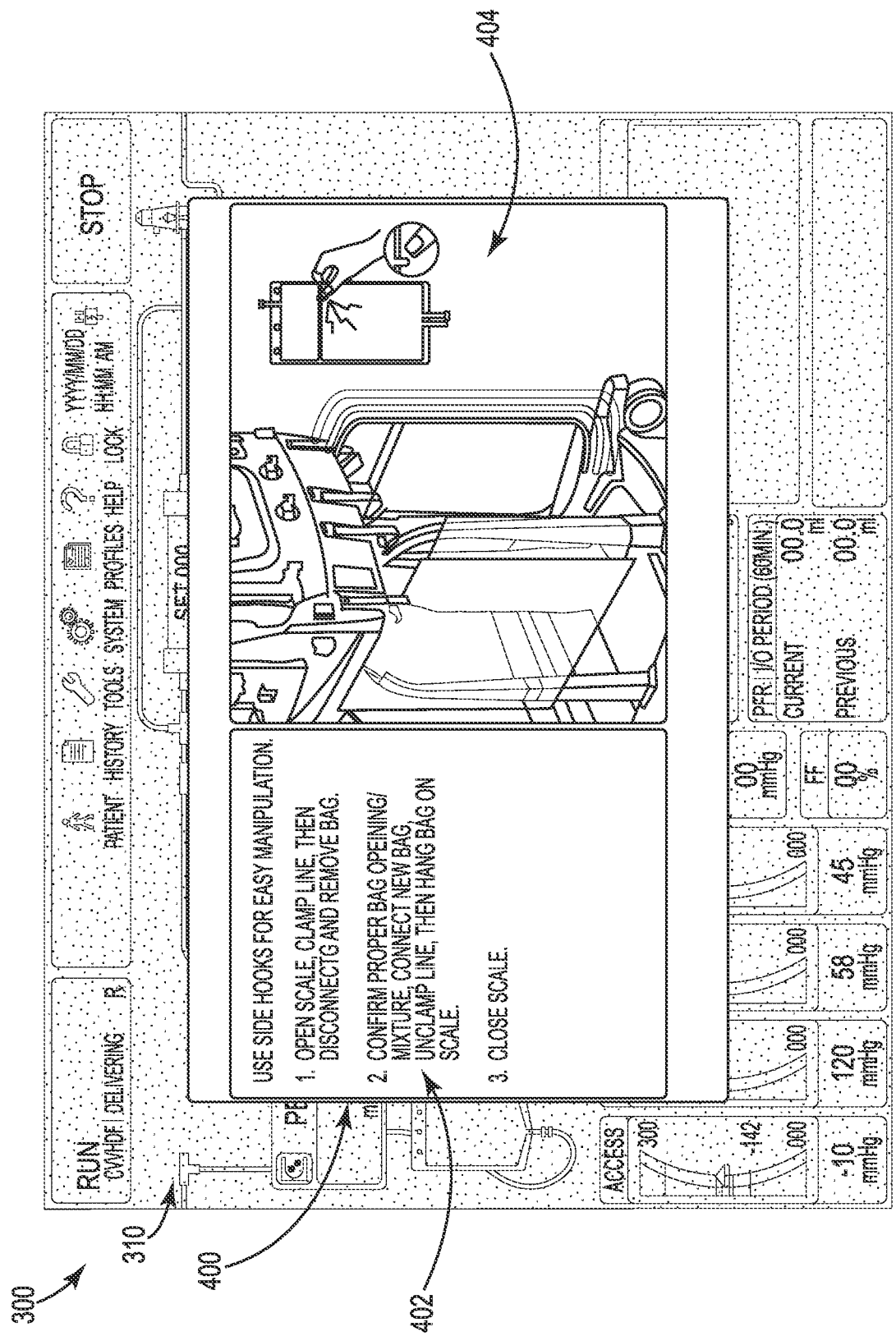

After selection, a reservoir change instruction region 400 may be depicted as shown in FIG. 15. Generally, the reservoir change instruction region 400 may include textual instructions 402 (e.g., alphanumeric strings, etc.) including the one or more steps to complete or perform a reservoir change and a graphical representation 404 of the present step.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the systems and methods described herein. Various modifications of the illustrative embodiments, as well as additional embodiments of the disclosure, will be apparent upon reference to this description.

What is claimed is:

1. An extracorporeal blood treatment system comprising:
   extracorporeal blood treatment apparatus for use in performing an extracorporeal blood treatment comprising:
      one or more pumps to move at least one of blood and a treatment solution during extracorporeal blood treatment, and
      one or more reservoirs to store one or more fluids during extracorporeal blood treatment;
   a display apparatus comprising a graphical user interface, wherein the graphical user interface is configured to depict a fluid region; and
   a computing apparatus operatively coupled to the extracorporeal blood treatment apparatus and the display apparatus, wherein the computing apparatus is configured to:
      perform an extracorporeal blood treatment;
      display on the graphical user interface a fluid region comprising at least one fluid area, wherein each of the at least one fluid area corresponds to a fluid and a reservoir of the one or more reservoirs storing the fluid, wherein the at least one fluid area comprises a pump element and a reservoir element, wherein the pump element comprises:
         a text identifier identifying the corresponding fluid; and
         a flow rate of the fluid during performance of the extracorporeal blood treatment,
      wherein the reservoir element comprises:
         an amount of the fluid within the reservoir storing the fluid during performance of the extracorporeal blood treatment; and
         an amount of time left before a reservoir change; and
      allow a user to select an element of the at least one fluid area to initiate an adjustment of the flow rate of the at least one selected fluid area.

2. The system of claim 1, wherein allowing a user to select an element of the at least one fluid area to initiate an adjustment of the flow rate of the at least one selected fluid area comprises allowing a user to select the pump element of the at least one fluid area to initiate an adjustment of the flow rate of the at least one selected fluid area.

3. The system of claim 1, wherein the computing apparatus is configured to display a rate adjustment area in response to selection of the at least one fluid area to initiate an adjustment of the flow rate of the at least one selected fluid area, wherein the rate adjustment area comprises one or more portions selectable by a user to adjust the flow rate of the corresponding fluid.

4. The system of claim 3, wherein the one or more portions of the rate adjustment area comprise a scrollable wheel scrollable by a user to adjust the flow rate.

5. The system of claim 3, wherein the one or more portions of the rate adjustment area comprise a rotary portion, the rotary portion comprising an outer portion movable by a user about the rotary portion to adjust the flow rate.

6. The system of claim 3, wherein the one or more portions of the rate adjustment area comprise an increment button to increase the flow rate and a decrement button to decrease the flow rate.

7. The system of claim 1, wherein the pump element defines a substantially rectangular shape.

8. The system of claim 1, wherein the pump element comprises a pump icon that is graphical depiction of a type of pump used for the corresponding fluid.

9. The system of claim 8, wherein the pump icon is graphical depiction of a peristaltic pump.

10. The system of claim 1, wherein the one or more reservoirs comprises a replacement fluid reservoir, an effluent reservoir, and a dialysate reservoir, wherein the one or more pumps comprises a replacement fluid pump operably coupled to the replacement fluid reservoir, an effluent pump operably coupled to the effluent reservoir, and a dialysate pump operably coupled to the dialysate reservoir, and
wherein the at least one fluid area comprises:
a replacement fluid area corresponding to replacement fluid;
an effluent fluid area corresponding to effluent; and
a dialysate fluid area corresponding to dialysate.

11. A method for an extracorporeal blood treatment system comprising:
performing an extracorporeal blood treatment;
providing a graphical user interface is configured to depict a fluid region;
displaying on the graphical user interface a fluid region comprising at least one fluid area, wherein each of the at least one fluid area corresponds to a fluid and a reservoir storing the fluid, wherein the at least one fluid area comprises a pump element and a reservoir element,
wherein the pump element comprises:
a text identifier identifying the corresponding fluid; and
a flow rate of the fluid during performance of the extracorporeal blood treatment,
wherein the reservoir element comprises:
an amount of the fluid within the reservoir storing the fluid during performance of the extracorporeal blood treatment; and
an amount of time left before a reservoir change; and
allowing a user to select an element of the at least one fluid area to initiate an adjustment of the flow rate of the at least one selected fluid area.

12. The method of claim 11, wherein allowing a user to select an element of the at least one fluid area to initiate an adjustment of the flow rate of the at least one selected fluid area comprises allowing a user to select the pump element of the at least one fluid area to initiate an adjustment of the flow rate of the at least one selected fluid area.

13. The method of claim 11, wherein the method further comprises displaying a rate adjustment area in response to selection of the at least one fluid area to initiate an adjustment of the flow rate of the at least one selected fluid area, wherein the rate adjustment area comprises one or more portions selectable by a user to adjust the flow rate of the corresponding fluid.

14. The method of claim 13, wherein the one or more portions of the rate adjustment area comprise a scrollable wheel scrollable by a user to adjust the flow rate.

15. The method of claim 13, wherein the one or more portions of the rate adjustment area comprise a rotary portion, the rotary portion comprising an outer portion movable by a user about the rotary portion to adjust the flow rate.

16. The method of claim 13, wherein the one or more portions of the rate adjustment area comprise an increment button to increase the flow rate and a decrement button to decrease the flow rate.

17. The method of claim 11, wherein the pump element defines a substantially rectangular shape.

18. The method of claim 11, wherein the pump element comprises a pump icon that is graphical depiction of a type of pump used for the corresponding fluid.

19. The method of claim 18, wherein the pump icon is graphical depiction of a peristaltic pump.

20. The method of claim 11, wherein the reservoir corresponding to each of the at least one fluid area comprises one of a replacement fluid reservoir, an effluent reservoir, and a dialysate reservoir, and
wherein the at least one fluid area comprises:
a replacement fluid area corresponding to replacement fluid;
an effluent fluid area corresponding to effluent; and
a dialysate fluid area corresponding to dialysate.

* * * * *